United States Patent [19]

Saksena et al.

[11] Patent Number: 5,403,937
[45] Date of Patent: Apr. 4, 1995

[54] PROCESS FOR PREPARING INTERMEDIATES FOR THE SYNTHESIS OF ANTIFUNGAL AGENTS

[75] Inventors: Anil K. Saksena, Upper Montclair; Viyyoor M. Girijavallabhan, Parsippany; Russell E. Pike, Stanhope; Haiyan Wang, Bayton; Raymond G. Lovey, West Caldwell; Yi-Tsung Liu, Morris Township, Morris County; Ashit K. Ganguly, Upper Montclair; William B. Morgan, Chatham Township, Morris County; Aleksey Zaks, Hoboken, all of N.J.

[73] Assignee: Schering Corporation, Kenilworth, N.J.

[21] Appl. No.: 55,268

[22] Filed: Apr. 30, 1993

[51] Int. Cl.$^6$ ............................................. C07D 249/08
[52] U.S. Cl. ................................................... 548/268.8
[58] Field of Search ........................... 548/266.6, 268.8

[56] References Cited

U.S. PATENT DOCUMENTS 5,039,676  8/1991  Saksena et al. ................. 548/266.6

FOREIGN PATENT DOCUMENTS 472392   2/1992  European Pat. Off. .
WO8904829 6/1989  WIPO .
WO9309114 5/1993  WIPO .

OTHER PUBLICATIONS

Evans et al., *J. Amer. Chem. Soc.*, 112, 8215–8216 (1990).
Evans et al., *J. Amer. Chem. Soc.*, 104, 1737–1739 (1982).
Evans et al., *J. Amer. Chem. Soc.*, 113, 1047–1049 (1991), with supplemental material.
Freifelder, *Catalytic Hydrogenation in Organic Synthesis*, pp. 120–121 (1978).
Oppolzer, et al, *J. Amer. Chem. Soc.*, 112, 2767–2772 (1990).
Evans, et al, *J. Amer. Chem. Soc.*, 103, 2127–2129 (1981).
Evans, et al., *Tetrahedron*, 44, 5525–5540 (1988).

*Primary Examiner*—Mary C. Lee
*Assistant Examiner*—Joseph K. McKane
*Attorney, Agent, or Firm*—Paul A. Thompson

[57] ABSTRACT

Disclosed is a process for preparing chiral compounds of the formula (I)

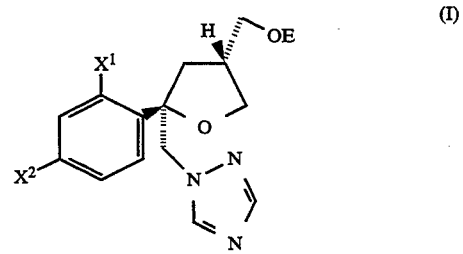

wherein: $X^1$ and $X^2$ are independently F or Cl; and E is $-SO_2R^2$, wherein $R^2$ is $C_1-C_6$ alkyl, $-C_6H_4CH_3$ or $-CF_3$; its enantiomer and racemates thereof, useful in the synthesis of tetrahydrofuran azole antifungals. Novel compounds of the formula

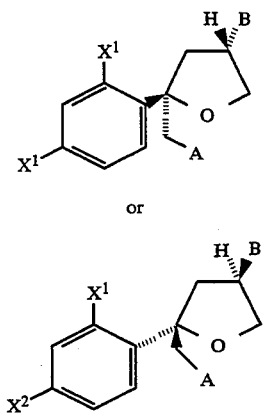

or wherein: $X^1$ and $X^2$ are independently F or Cl; B represents $-C(O)Q^*$ or $-CH_2OR''$; $Q^*$ represents a chiral auxiliary group; $R''$ represents a hydroxy protecting group selected from $-CH_2C_6H_5$, or $-C(O)R^1$, wherein $R^1$ is $C_1-C_6$ alkyl; and A represents Cl, Br, I or triazolyl; are also disclosed.

16 Claims, No Drawings

PROCESS FOR PREPARING INTERMEDIATES FOR THE SYNTHESIS OF ANTIFUNGAL AGENTS

BACKGROUND OF THE INVENTION

The present invention comprises a process for preparing chiral intermediates useful in the preparation of tri-substituted tetrahydrofuran azole antifungals.

PCT International Publication Number WO 89/04829, published 1 Jun. 1990, and U.S. Pat. No. 5,039,676 (A. K. Saksena et al.) discloses (±) cis and (±) trans antifungal compounds represented by the formula

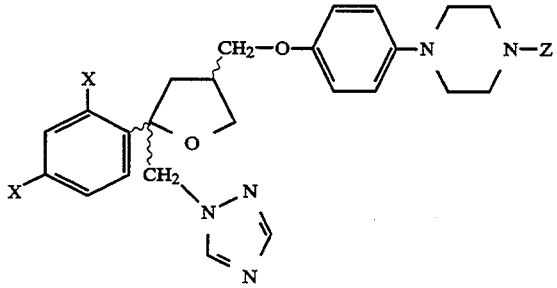

wherein X=F, Cl; Z=loweralkyl, (C$_2$-C$_8$) alkanoyl or phenyl substituted by 2-loweralkyl-3-oxo-1,2,4-triazol-4-yl, e.g., (±)-cis and (±)-trans-1-[4-[[2-(2,4-difluorophenyl)-2-[(1H-1,2,4-triazol-1-yl)methyl]tetrahydro-4-furanyl]methoxy]phenyl]-4-(1-methylethyl)piperazine.

In addition, PCT International Application No. PCT/US92/08981 relates to antifungal compounds of the formula

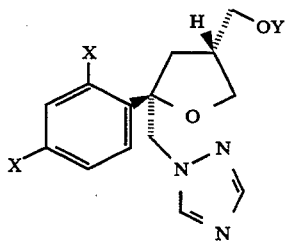

wherein:
X is independently both F or both Cl or one X is independently F and the other is Cl;
Y is

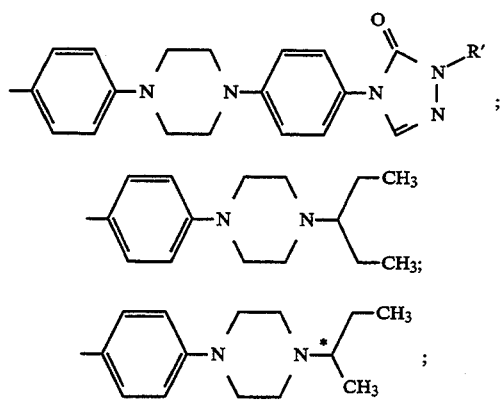

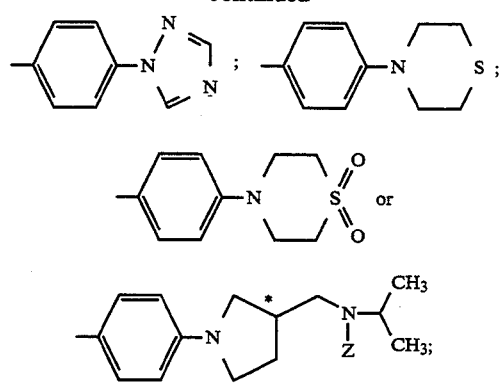

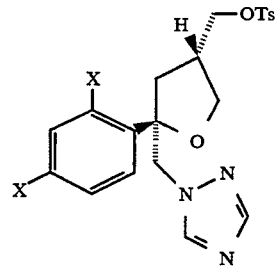

wherein:
R'=(C$_1$-C$_{10}$)alkyl; (C$_2$-C$_{10}$)alkenyl; (C$_2$-C$_{10}$)alkynyl; (C$_3$-C$_8$)cycloalkyl; or CH$_2$R$^2$;
R$^2$=(C$_1$-C$_3$) perhaloalkyl; CO$_2$R$^3$; *CH(OR$^4$)CH$_2$OR$^4$ or CH$_2$N(R$^5$)$_2$
R$^3$=lower alkyl or H
R$^4$=R$^3$ or (CH$_2$)$_2$OR$^3$
R$^5$=lower alkyl
Z=H, or (C$_1$-C$_5$) alkanoyl and the carbons with the asterisk (*) have the R or S absolute configuration; or a pharmaceutically acceptable salt thereof.

PCT/US92/08981 further discloses processes for the synthesis of tri-substituted tetrahydrofuran azole antifungals via a tosylate intermediate of the formula

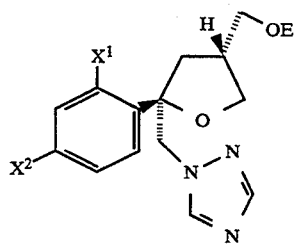

wherein X is as defined above.

The prior art process for preparing the tosylate intermediate is inefficient and requires a costly chiral epoxidation to introduce the proper stereochemistry in the molecule. It was therefore desirable to develop a chiral synthesis of this key intermediate which does not suffer the shortcomings of the prior art process

SUMMARY Of THE INVENTION

The present invention comprises a process for preparing compounds of the formula (I)

(I)

wherein: $X^1$ and $X^2$ are independently F or Cl; and E is —$SO_2R^2$, wherein $R^2$ is $C_1$-$C_6$ alkyl, —$C_6H_4CH_3$ or —$CF_3$; comprising the steps:

(a) cyclizing a chiral alcohol of the formula (II)

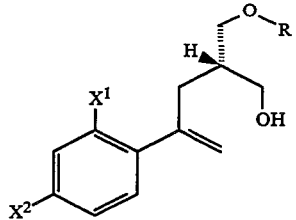

(II)

wherein $X^1$ and $X^2$ are as defined above, and R is a hydroxy protecting group selected from —$CH_2$—$C_6H_5$, tetrahydropyran-2-yl or —$C(O)R^1$, wherein $R^1$ is $C_1$-$C_6$ alkyl, by treating with a halogen and a base to form a chiral halide of the formula (III)

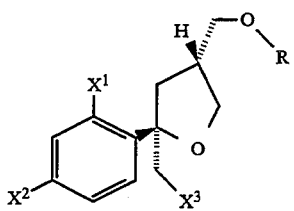

(III)

wherein $X^1$, $X^2$ and R are as defined above, and $X^3$ is Cl, Br or I; and (b) treating the halide of formula (III) of step (a) with an alkali metal triazole to form a chiral triazole compound of the formula I, wherein $X^3$ is triazolyl; removing the protecting group R from the triazole compound to form an alcohol of the formula (III), wherein $X^3$ is triazolyl and R is H; and treating the alcohol with a compound of the formula E—X, wherein X is Cl or Br, and E is as defined above, to form the compound of formula (I); or (bi) removing the protecting group R from the halide of formula (III) of Step (a) to form an alcohol, wherein R is H; treating the alcohol with an alkali metal triazole to form a chiral triazole compound of the formula (III), wherein $X^3$ is triazolyl and R is H; and treating the alcohol with a compound of the formula E—X, wherein X is Cl or Br, and E is as defined above, to form the compound of formula (I).

The present invention further comprises a process, designated Process A, wherein R is —$C(O)R^1$, and the starting compound of formula (II) of Step (a) is prepared by selectively esterifying a prochiral diol of the formula (IV)

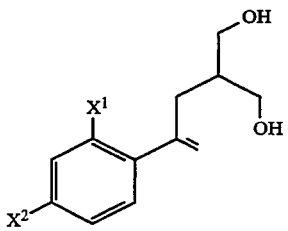

(IV)

with an effective amount of a mild acylating agent in the presence of an enzyme to form a chiral hydroxy ester of the formula (IIa)

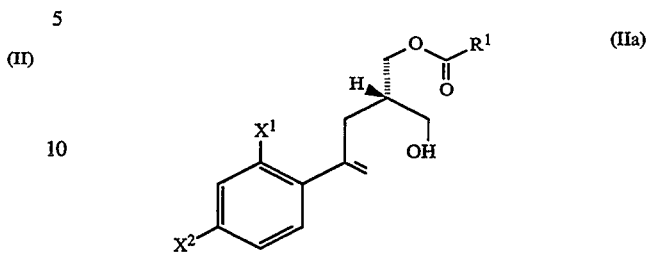

(IIa)

wherein $X^1$, $X^2$ are as defined above and $R^1$ is $C_1$-$C_6$ alkyl.

Alternatively, the selective esterification of the prochiral diol of formula (IV) is achieved via a process comprising the steps:

(i) esterifying the prochiral diol of formula (IV) with an amount of an acylating agent effective to form a diester of the formula (V)

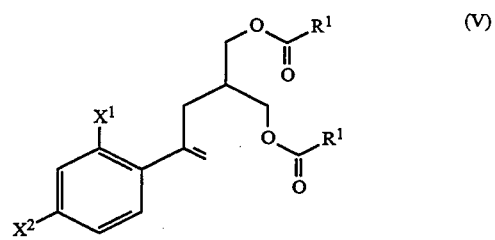

(V)

wherein $X^1$, $X^2$ and $R^1$ are as defined above; and (ii) stereoselectively hydrolyzing the diester of formula (V) of step (i) in the presence of an enzyme to form a chiral hydroxy ester of the formula (IIa)

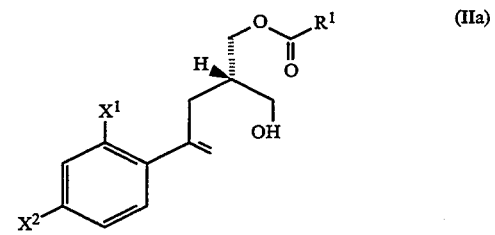

(IIa)

wherein $X^1$, $X^2$ and $R^1$ are as defined above.

The present invention also further comprises a process according to Process A wherein the prochiral diol of formula (IV) is prepared via a process comprising the steps:

(A1) converting an allylic alcohol of the formula (VI)

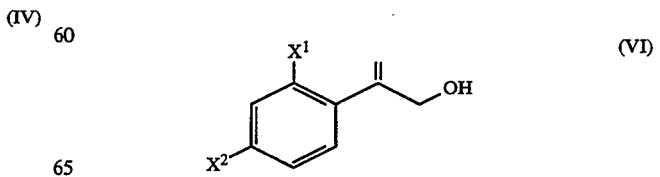

(VI)

wherein $X^1$ and $X^2$ are as defined above, to a compound of the formula (VII)

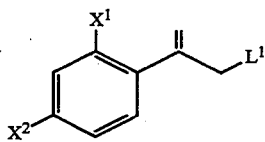

wherein $X^1$ and $X^2$ are as defined above and $L^1$ is a leaving group selected from Br, $-OSO_2CH_3$ and $-OSO_2C_6H_4CH_3$;

(A2) reacting the compound of formula (VII) of Step (A1) with an amount of an alkali metal salt of the anion derived from a di($C_1$-$C_6$ alkyl)malonate effective to form a diester of the formula (VIII)

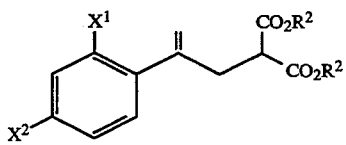

wherein $X^1$ and $X^2$ are as defined above, and $R^2$ is $C_1$-$C_6$ alkyl;.

(A3) treating the diester of formula (VIII) of Step (A2) with an amount of a hydride reducing agent effective to form the prochiral diol of formula (IV).

In an alternative embodiment, designated Process B, the present invention comprises a process for preparing chiral compounds of formula (II), wherein R is $-CH_2-C_6H_5$, for use in preparing compounds of the formula (I), comprising the steps:

(B1) reacting a compound of the formula (IX)

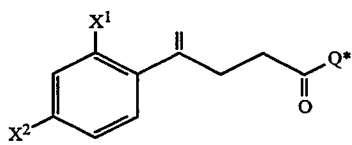

wherein $X^1$ and $X^2$ are as defined above and $Q^*$ is a chiral auxiliary group, with a compound of the formula $C_6H_5CH_2-O-CH_2L$, wherein L is a leaving group selected from Cl, Br and I, in the presence of $TiCl_4$ and a tertiary amine base, in amounts effective to form a chiral compound of the formula (X)

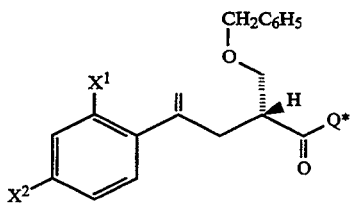

wherein $X^1$, $X^2$ and $Q^*$ are as defined above; and (B2) treating the product of formula (X) of Step (B1) with an amount of $LiAlH_4$ effective to form a chiral compound of the formula (II), wherein R is $-CH_2C_6H_5$.

The present invention further comprises a process according to Process B wherein the starting compound of the formula (IX)

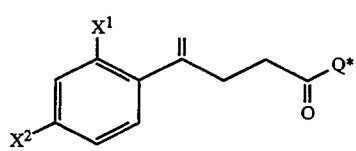

is prepared by a process comprising the steps:

(B3) heating an allylic alcohol of the formula (VI)

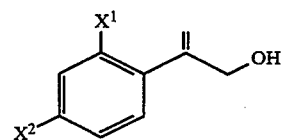

wherein $X^1$ and $X^2$ are as defined above, with an effective amount of an orthoester of the formula $CH_3C(OR^1)_3$, wherein $R^1$ is as defined above, and a catalytic amount of $C_2H_5CO_2H$, followed by treatment with an amount of a hydroxide base effective to form an acid of the formula (XI)

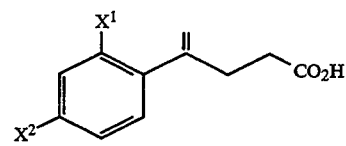

wherein $X^1$ and $X^2$ are as defined above; and (B4) treating the acid of formula (XI) of step (B3) with an effective amount of an activating agent, then with an alkali metal salt of the formula $M^+$ $^-Q^*$, wherein $M^+$ is an alkali metal cation and $^-Q^*$ is the anion derived from a compound of the formula $HQ^*$, wherein $Q^*$ is as defined above, to form a compound of the formula In a second alternative embodiment, designated Process C, the present invention comprises a process for preparing compounds of the formula (I) wherein the chiral halide of formula (III) of Step (a), wherein R is H, is prepared by a process comprising the steps:

(C1) treating a compound of the formula (IX), as defined above, with effective amounts of S-trioxane, $TiCl_4$ and a tertiary amine base to form a chiral compound of the formula (XII)

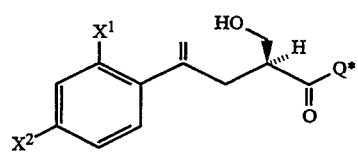

wherein $X^1$, $X^2$ and $Q^*$ are as defined above;

(C2) cyclizing a compound of the formula (XII) of Step (C1) by treating with effective amounts of a halogen and a base to form a chiral halide of the formula (XIII)

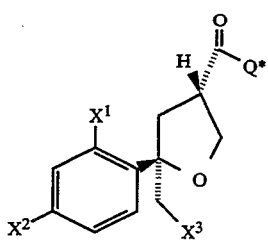
(XIII)

wherein $X^1$, $X^2$, $X^3$ and $Q^*$ are as defined above;

(C3) treating the chiral halide of formula (XIII) of Step (C3) with an amount of a hydride reducing agent effective to form a chiral halide of the formula (III), wherein R is H.

The process of the present invention can also be used to prepare compounds of the formula (XIV)

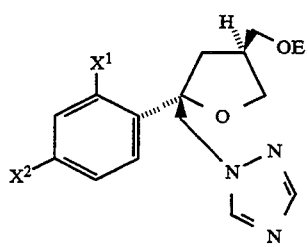
(XIV)

wherein $X^1$, $X^2$ and E are as defined above, i.e., enantiomers of compounds of the formula (I), by utilizing a chiral auxiliary of the opposite configuration, or by the choice of an enzyme which selectively produces the R-enantiomer of a compound of the formula (II), e.g. a compound of the formula (XV)

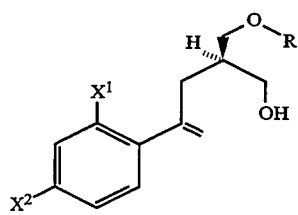
(XV)

wherein $X^1$, $X^2$ and R are as defined above.

The present invention further comprises a process for converting compounds of the formula (XV) to compounds of the formula (II) by protection of the free hydroxy group using a suitable protecting group $R^a$, and selective hydrolysis of the —OR group to form an alcohol of the formula (XVI)

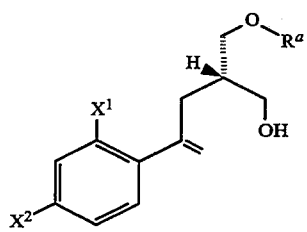
(XVI)

wherein $X^1$ and $X^2$ are as defined above and $R^a$ is a hydroxy protecting group. Preferably $R^a$ is a hydroxy protecting group selected from —CH$_2$C$_6$H$_5$, tetrahydropyran-2-yl or —C(O)R$^1$, wherein R$^1$ is as defined above, provided that R≠$R^a$, in which case compounds of formula (XVI) are compounds of the formula (II).

In an alternative embodiment, the process of the present invention further comprises a process designated Process D for preparing a compound of the formula (I) wherein the chiral iodide of Step (a), being a compound of the formula (III) wherein R is —C(O)R$^1$, wherein R$^1$ is C$_1$-C$_6$ alkyl, is prepared by a process comprising the steps:

(D1) esterifying a chiral alcohol of the formula (II)

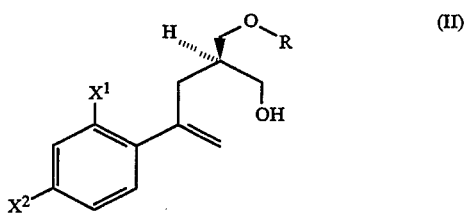
(II)

wherein $X^1$ and $X^2$ are as defined above, and R is —CH$_2$—C$_6$H$_5$, by treating with an effective amount of an acylating agent to form a chiral compound of the formula (XIX)

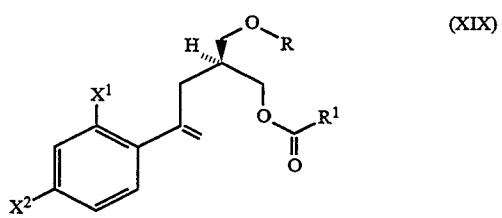
(XIX)

wherein $X^1$, $X^2$ and R are as defined above and $R^1$ is C$_1$-C$_6$ alkyl; and (D2) cyclizing the chiral product of formula (XIX) of Step (D1) by treating with a halogen to form a chiral halide of the formula (III)

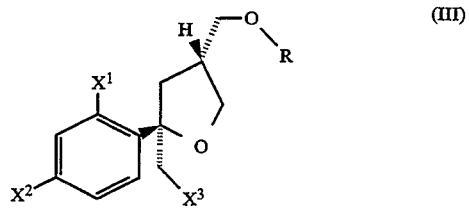
(III)

wherein $X^1$, $X^2$ are as defined above, R is —C(O)R$^1$, R$^1$ is as defined above and $X^3$ is Cl, Br or I.

The present invention also further comprises chiral compounds of the formula (XVII) or (XVIII)

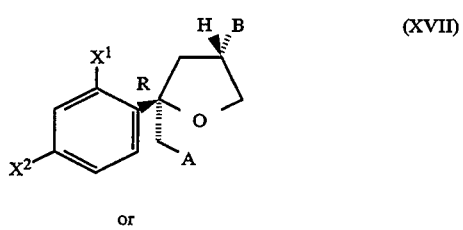
(XVII)

or

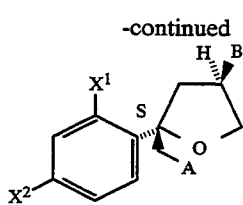 (XVIII)

wherein:
X¹ and X² are independently F or Cl;
B represents —C(O)Q*—CH₂OR";
Q* represents a chiral auxiliary group selected from chiral oxazolidinones of the formula

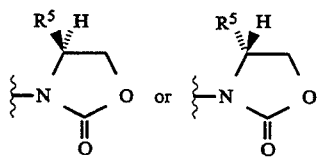

wherein R⁵ is isopropyl or benzyl, and chiral sultams of the formula

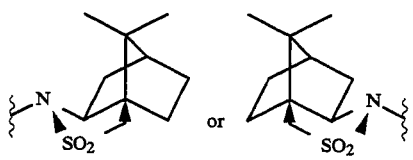

R" represents a hydroxy protecting group selected from —CH₂C₆H₅, or —C(O)R¹, wherein R¹ is C₁-C₆ alkyl; and
A represents Cl, Br, I or a triazole of the formula

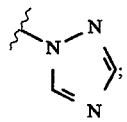

useful as intermediates for preparing tetrahydrofuran azole antifungal agents.

The process of the present invention is chemically efficient and produces chiral compounds of the formula I in high optical purity. Therefore, the instantly claimed process does not suffer the shortcomings of the prior art process.

The process of the present invention can also be used to prepare compounds of the formula I in racemic form by utilizing the achiral diol IV in place of a chiral compound of the formula II for the cyclization of Step (a) forming a racemic iodide of formula III wherein R is H. No deprotection is necessary in Step (b) where an iodide III, wherein R is H, is used.

DETAILED DESCRIPTION

The process of the present invention utilizes a chiral auxiliary group, or alternatively an enzyme, to stereoselectively produce chiral compounds from achiral starting materials. The stereochemical designations represented by     and     bonds denote both absolute stereochemistry and, where more than one chiral center is present, relative stereochemistry. The optical purity of compounds is generally given in terms of the enantiomeric excess (e.e.) of the indicated stereoisomer.

In the process of the present invention, where a chiral auxiliary is used to form a single enantiomer of a compound, the opposite enantiomer can be prepared by utilizing the opposite enantiomer of the chiral auxiliary employed. Similarly, where an enzyme is used to prepare a chiral compound from a prochiral starting material, the specific enantiomer obtained is controlled by selection of the proper enzyme.

As used herein the term "alkyl" means a straight or branched alkyl chains of 1 to 6 carbon atoms;

"hydroxide base" means LiOH, KOH, NaOH, Ca(OH)₂;

"base" means pyridine, NH₄OH, Na₂CO₃, K₂CO₃, NaHCO₃ or KHCO₃;

"tertiary amine base" means Et₃N or Hünigs base;

"alkali metal triazole" means an alkali metal salt of the anion derived from triazole, e.g., sodium triazole, potassium triazole, lithium triazole;

"hydride reducing agent" means LiAlH₄, NaBH₄, LiBH₄, NaBH₃CN;

"halogen" means Cl₂, Br₂ or I₂, and "halide" means a chloride, bromide or iodide anion;

"brominating agent" means a reagent capable of converting an alcohol to a bromide, preferably PBr₃;

"activating agent" means a reagent capable of converting a carboxylic acid into a reactive derivative, such as an acid halide, anhydride or a mixed anhydride, preferably reagents such as SOCl₂, oxalyl chloride, carbonylditriazole or oxalylditriazole;

"alkali metal salt" means a salt comprising a cation derived from Li, Na or K, and an anion;

"sulfonylating agent" means a reagent capable of converting an —OH group into a sulfonyl group of the formula —OSO₂R⁴, wherein R⁴ is C₁-C₆ alkyl, or —C₆H₄CH₃, preferably a reagent such as tosyl chloride or mesyl chloride "leaving group" means a substituent which is readily displaced by a nucleophile, such as Cl, Br, I, —OSO₂CH₃ or —OSO₂C₆H₄CH₃;

"acylating agent" means a reagent of the formula R¹—C(O)—Z, wherein R¹ is C₁-C₆ alkyl, and Z is a suitable leaving group, such that said acylating agent is capable of reacting with the hydroxy group of an alcohol to form an ester; preferred are acylating agents selected from acid chlorides, acid anhydrides or mixed anhydrides, and most preferably a reagent such as butyric anhydride, acetyl chloride or acetic anhydride;

"mild acylating agent" means a reagent that is used in combination with an enzyme to transfer an acyl group to a substrate bearing a hydroxy group; such reagents include: esters of the formula R¹—C(O)—OR³, wherein R³ is trifluoroethyl, C₁-C₆ alkyl or C₁-C₆ alkenyl, and preferably the ester is vinyl butyrate, vinyl acetate, isopropenyl acetate, methyl acetate, ethyl acetate, isopropyl acetate, trifluoroethyl acetate, trifluoroethyl butyrate, trifluoroethyl isobutyrate or trifluoroethyl 2-methylbutyrate, with vinyl acetate being most preferred; and acetic anhydride.

Enzymes for use in the present invention are selected from enzymes capable of stereoselectively hydrolyzing a symmetrical prochiral diester, or alternatively catalyzing the esterification of a symmetrical prochiral diol, such that a single chiral hydroxy ester is formed in high e.e. Enzymes for use in the process of the present invention include the following commercially available enzyme preparations: Amano acylase; Amano AK; Amano AP-12; Amano AY-30; Amano CE; Amano CES; Amano D; Amano FAP-15; Amano G; Amano GC-4; Amano MAP-10; Amano N; Amano PGE; Amano PS-30; Amano R; Biocatalyst Alcaligenes sp.; Biocatalyst *Asp. niger*, Biocatalyst *C. cylindracea;* Biocatalyst *Chr. viscosum;* Biocatalyst *H. lanuglosa;* Biocatalyst *M. javanicus;* Biocatalyst *M. meihei;* Biocatalyst *P. cyclopium;* Biocatalyst *Ps. fluorescens;* Biocatalyst *Rh. japonicus;* Biocatalyst *Rh. javanicus;* Biocatalyst *Rh. niveus;* Genzyme *C. cylindracea;* Gist Brocades Calf lipase; Gist Brocades Kid lipase; IBT Peptidase; ISC BE1; ISC BP1; ISC BP1 immob; ISC BP2; ISC BP2 immob; ISC BP3; ISC BP4; ISC BPG1; ISC FP1; Lilipase A-10; Meito MY; Meito OF; Meito PL; Novo IM20; Novo SP435; Sigma PPL; Sigma Wheatgerm; Solvay PPL; Toyobo LPL; and Toyobo NEP-160. The preferred enzymes are porcine pancreatic lipase, Amano CE (*Humicloa lanugiosa*), Amano AY-30, Biocatalysts *H. lanugiosa*, Biocatalysts *M. meihei*, Biocatalysts *Ps. fluorescens*, Meito MY, Meito PL, Novo Lipozyme IM-20, and Novo SP435 (*Candida antartica*). Most preferred are Amano CE and Novo SP435.

The chiral auxiliary "Q*" is a chiral oxazolidinone of the formula

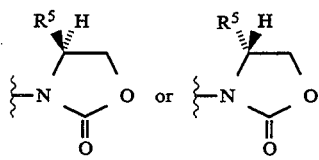

wherein $R^5$ is isopropyl or benzyl, as disclosed by Evans et al, in *J. Amer. Chem. Soc.*, 103, 2127–2129 (1981) and *Tetrahedron*, 44, 5525–5540 (1988); or a chiral sultam of the formula

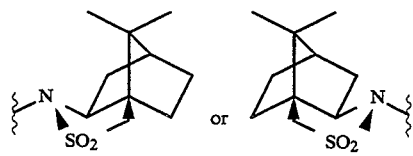

as disclosed by Oppolzer et al, *J. Amer. Chem. Soc.*, 112, 2767–2772 (1990).

As used herein the following reagents and solvents are identified by the abbreviations indicated: methanol (MeOH); tetrahydrofuran (THF); diethyl ether (Et$_2$O); lithium di-isopropylamide (LDA); triethylamine (Et$_3$N); di-isopropylethylamine (Hünigs base); ethyl acetate (EtOAc); ethanol (EtOH); N,N-dimethylformamide (DMF); N,N'-dimethylpropyleneurea (DMPU); 4-dimethylaminopyridine (DMAP); p-toluenesulfonyl chloride (tosyl chloride or TsCl); methanesulfonyl chloride (mesyl chloride or MsCl); p-toluenesulfonic acid (p-TSA)

The following abbreviations are used to identify substituent groups in the structural formulae: tetrahydropyran-2-yl radical (THP); p-toluenesulfonyl radical (Ts); and acetyl radical (Ac).

The present invention comprises a process for preparing a compound of the formula I as shown in Reaction Scheme 1.

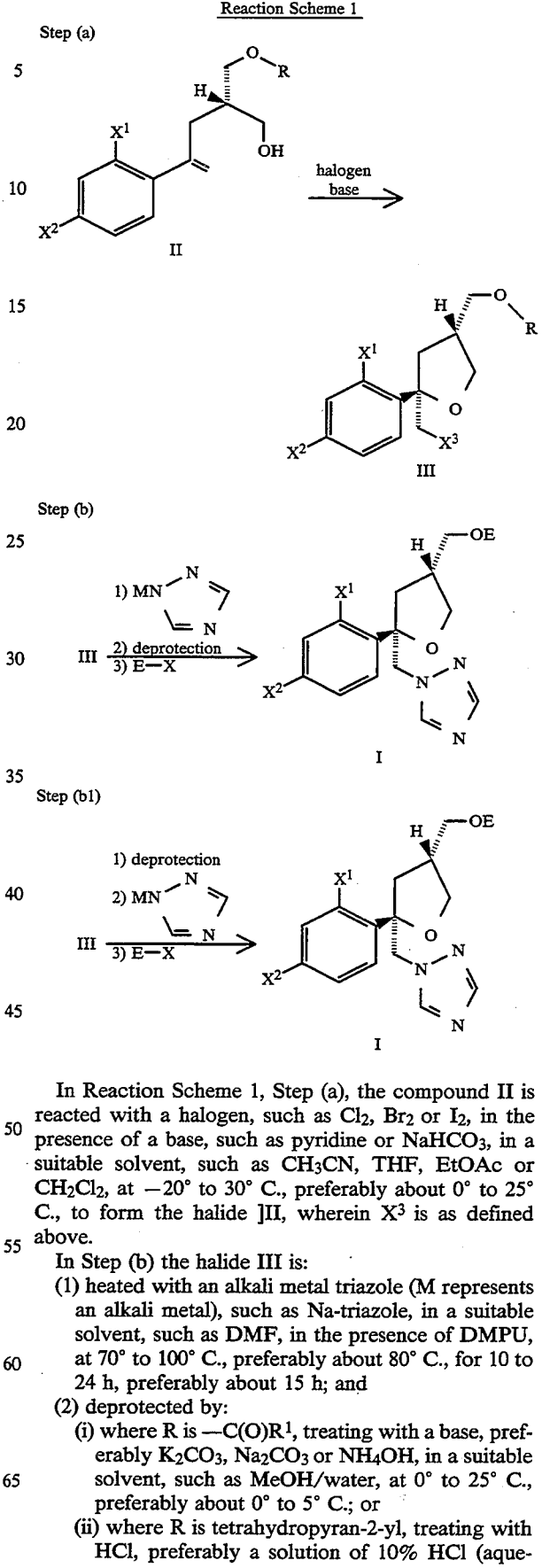

In Reaction Scheme 1, Step (a), the compound II is reacted with a halogen, such as Cl$_2$, Br$_2$ or I$_2$, in the presence of a base, such as pyridine or NaHCO$_3$, in a suitable solvent, such as CH$_3$CN, THF, EtOAc or CH$_2$Cl$_2$, at −20° to 30° C., preferably about 0° to 25° C., to form the halide III, wherein X$^3$ is as defined above.

In Step (b) the halide III is:
(1) heated with an alkali metal triazole (M represents an alkali metal), such as Na-triazole, in a suitable solvent, such as DMF, in the presence of DMPU, at 70° to 100° C., preferably about 80° C., for 10 to 24 h, preferably about 15 h; and
(2) deprotected by:
  (i) where R is —C(O)R$^1$, treating with a base, preferably K$_2$CO$_3$, Na$_2$CO$_3$ or NH$_4$OH, in a suitable solvent, such as MeOH/water, at 0° to 25° C., preferably about 0° to 5° C.; or
  (ii) where R is tetrahydropyran-2-yl, treating with HCl, preferably a solution of 10% HCl (aqueous), at 15° to 35°, preferably about 25° C., for 1 to 6 h, preferably about 3 h; or (iii) where R is —CH$_2$C$_6$H$_5$, hydrogenating under H$_2$ atmosphere in a suitable solvent, such as EtOH, in the presence of a suitable catalyst, such as Pd on carbon, preferebly 10% Pd on carbon, and an acid, preferably HCl;

to form an alcohol wherein R is H; and (3) treated with a compound of the formula E—X, wherein X is a halide, preferably chloride, in the presence of a base, such as pyridine, to form a compound of the formula I.

In the alternative Step (b1), the halide III is:

(1) deprotected by:
   (i) where R is —C(O)R$^1$, treating with a base, preferably K$_2$CO$_3$, Na$_2$CO$_3$ or NH$_4$OH, in a suitable solvent, such as MeOH/water, at 0° to 25° C., preferably about 0° to 5° C.; or
   (ii) where R is tetrahydropyran-2-yl, treating with HCl, preferably a solution of 10% HCl (aqueous), at 15° to 35°, preferably about 25° C., for 1 to 6 h, preferably about 3 h; or
   (iii) where R is —CH$_2$C$_6$H$_5$, hydrogenating under H$_2$ atmosphere in a suitable solvent, such as EtOH, in the presence of a suitable catalyst, such as Pd on carbon, preferebly 10% Pd on carbon, and an acid, preferably HCl, according to the procedure disclosed by Freifelder, in "Catalytic Hydrogenation in Organic Synthesis, Procedures and Comments", p. 120, J. Wiley & Sons (1978);

to form an alcohol wherein R is H; and (2) the alcohol is heated with an alkali metal triazole (M represents an alkali metal), such as Na-triazole, in a suitable solvent, such as DMF, in the presence of DMPU, at 70° to 100° C., preferably about 80° C., for 10 to 24 h, preferably about 15 h; and (3) treated with a compound of the formula E—X, wherein X is a halide, preferably chloride, in the presence of a base, such as pyridine, to form a compound of the formula I.

In the embodiment of Process A, the present invention further comprises a process wherein the chiral compound of formula (II) is a chiral hydroxy ester of the formula (IIa), i.e., a compound of the formula (II) wherein R is —C(O)R$^1$ and R$^1$ is as defined above. The chiral hydroxy ester of formula (IIa) is prepared from a prochiral diol of the formula (IV) by using an enzyme to selectively esterify the prochiral diol (IV), thus forming the chiral compound of formula (IIa). The selective esterification is accomplished according to the process shown in Reaction Scheme A.

Reaction Scheme A

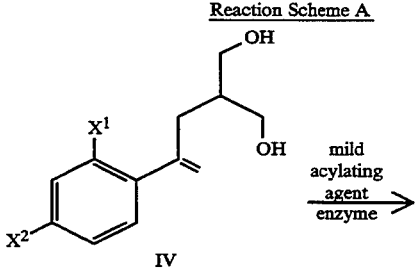

-continued
Reaction Scheme A

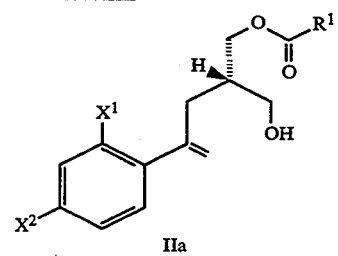

In Reaction Scheme A, the prochiral diol IV is treated with a mild acylating agent, preferably an ester of the formula R$^1$—C(O)—OR$^3$, wherein R$^1$ is as defined above and R$^3$ is C$_1$-C$_6$ alkyl, most preferably vinyl acetate, in the presence of an enzyme, most preferably Novo SP435, in a suitable solvent, such as toluene or CH$_3$CN, at 0° to 35° C., preferably about 25° C., to form the chiral hydroxy ester of the formula IIa.

By utilizing other lipase enzymes, such as Amano CE, in the process of Reaction Scheme A, the R-enantiomer, i.e., a compound of the formula XV, as defined above, can be prepared.

The chiral hydroxy ester IIa is alternatively prepared by the process of Reaction Scheme AA.

Reaction Scheme AA

Step (a)

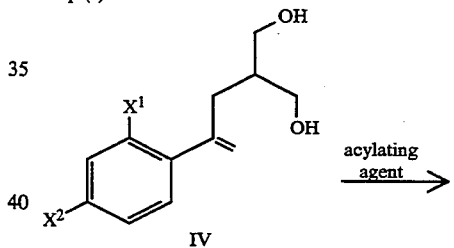

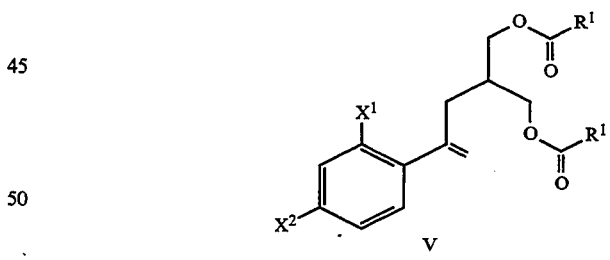

Step (b)

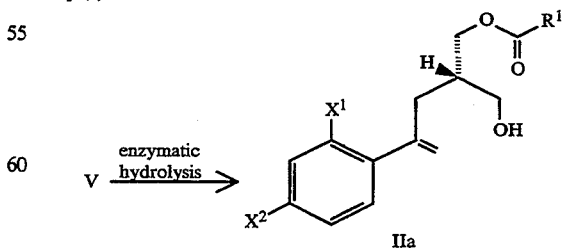

In Reaction Scheme AA, Step (a), the prochiral diol IV is treated with an acylating agent, preferably an acid halide, acid anhydride or mixed anhydride, most preferably butyric anhydride, acetyl chloride or acetic anhydride, in a suitable solvent, such as THF, at 0° C. to 40° C., preferably about 25° C., to form the diester V.

In Step (b), the diester V is treated with an enzyme, preferably a lipase, most preferably Amano CE, in a suitable solvent, such as THF/water, at 15° to 35° C., preferably about 25° C., to form the chiral hydroxy ester IIa.

The present invention further comprises a process according to Process A wherein the prochiral diol IV is prepared by the process described in Reaction Scheme AAA.

about 25° C., for 1 to 4 h, preferably about 2 h, to form the prochiral diol IV.

Alternatively in Step (A3), the diester VIII is treated with NaBH$_4$, in the presence of LiCl, in a suitable solvent, such as EtOH, at 0° to 35° C., preferably 0° to 25° C., for 1 to 4 h, preferably about 1½h, form the prochiral diol IV.

In the alternative embodiment of Process B, the present invention comprises a process wherein the chiral compound of formula (II) is a chiral benzyl ether of the formula (IIb), i.e., a compound of the formula (II) wherein R is —CH$_2$C$_6$H$_5$. The chiral benzyl ether of formula (IIb) is prepared by the process shown in Reaction Scheme B.

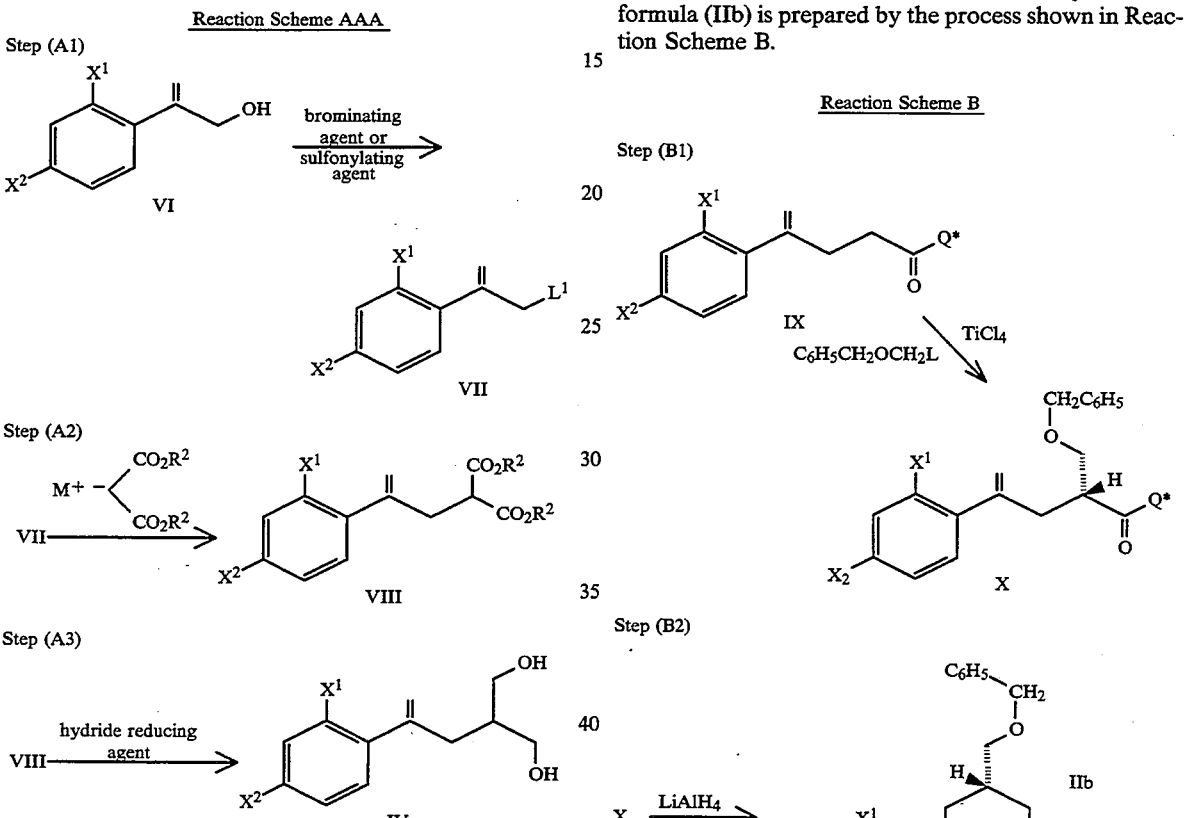

In Reaction Scheme AAA, Step (A1), the allylic alcohol VI is treated with a brominating agent, preferably PBr$_3$, in a suitable solvent, such as CH$_2$Cl$_2$, at −10° to 35° C., preferably at 0° to 25° C., for 30 to 90 min, preferably about 1 h, to form an allylic bromide, i.e., a compound of formula VII, wherein L$^1$ is Br.

Alternatively, in Step (A1), the allylic alcohol V1 is treated with a sulfonylating agent, such as mesyl chloride or tosyl chloride, a tertiary amine base, such as Et$_3$N, and DMAP, in a suitable solvent, such as CH$_2$Cl$_2$, at −10° to 35° C., preferably 0° to 25° C., to form the sulfonylated product, i.e., a compound of the formula VII wherein L$^1$ is —OSO$_2$CH$_3$ or —OSO$_2$C$_6$H$_4$CH$_3$.

In Step (A2), the compound of formula VII is treated with an alkali metal salt of the anion derived from di(C$_1$-C$_6$ alkyl)malonate, preferably NaCH(CO$_2$C$_2$H$_5$)$_2$, in a suitable solvent, such as THF, at 15° to 35°, preferably about 25° C., for 1 to 3 h, preferably about 1.5 h, to form the diester VIII.

In Step (A3), the diester VIII is treated with a hydride reducing agent, preferably LiAlH$_4$, in a suitable solvent, such as THF or Et$_2$O, at 0° to 35°, preferably In Reaction Scheme B, Step (B1), a compound of the formula IX is treated with TiCl$_4$ and a compound of the formula C$_6$H$_5$CH$_2$OCH$_2$L, wherein L is a leaving group, preferably a halide, in the presence of a tertiary amine base, such as Et$_3$N, at −10° to 10° C., preferably about 0° C., to form a chiral compound of the formula X.

In Step (B2), the chiral compound of formula X is treated with LiAlH$_4$ in a suitable solvent, such as THF or Et$_2$O, at 0° to 35° C., preferably about 25° C., to form the chiral benzyl ether IIb.

The present invention further comprises a process according to Process B wherein the compound of the formula IX: is prepared by the process described in Reaction Scheme BB.

Reaction Scheme BB

Step (B3)

-continued
Reaction Scheme BB

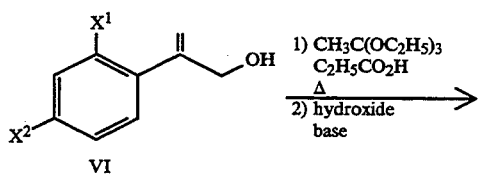

VI

Step (B4)

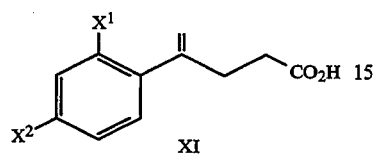

XI

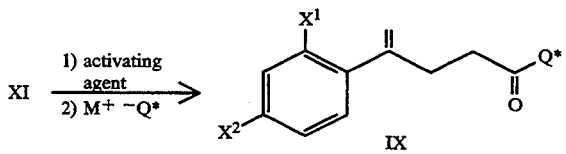

In Reaction Scheme BB, Step (B3), the allylic alcohol VI is treated with $CH_3C(OC_2H_5)_3$ and a catalytic amount of propionic acid at 90° to 130° C., preferably about 120° C., then treated with a hydroxide base, preferably KOH or NaOH, in a suitable solvent, such as MeOH, preferably MeOH/water, at 15° to 35° C., preferably about 25° C., to form the acid XI.

In Step (B4), the acid XI is treated with an activating agent, preferably $SOCl_2$ or oxalyl chloride, at 15° to 35° C., preferably about 25° C., to form a reactive derivative, such as an acid chloride. The reactive derivative is treated with an alkali metal salt of the formula $M^+\,^-Q^*$, preferably the Li+ salt, wherein $^-Q^*$ is preferably an anion derived from a chiral oxazolidinone of the formula

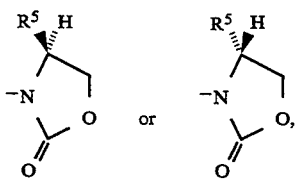

at $-70°$ to 25° C., preferably $-70°$ to 0° C., to form the compound of formula IX.

In the second alternative embodiment of Process C, the present invention comprises a process wherein the chiral halide of formula (III) is a chiral alcohol of the formula (IIIa), i.e., a compound of the formula (III) wherein R is H. The alcohol of formula (IIIa) is prepared by the process shown in Reaction Scheme C.

Reaction Scheme C

Step (C1)

-continued
Reaction Scheme C

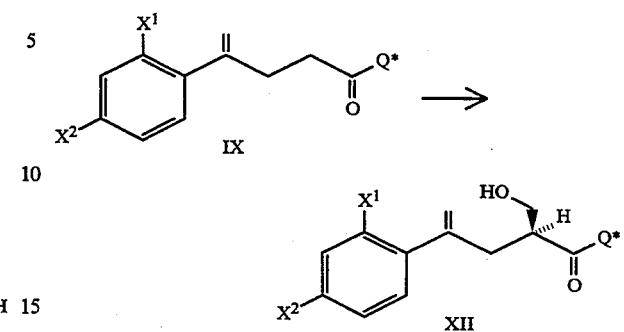

Step (C2)

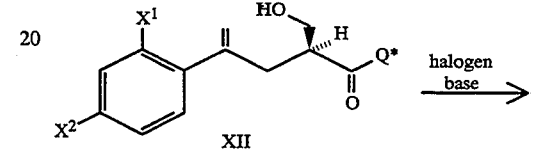

Step (C3)

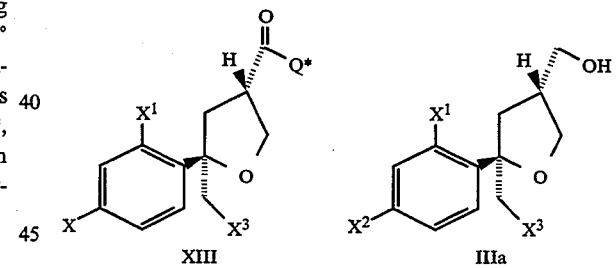

In Reaction Scheme C, Step (C1), the compound of the formula IX is converted to the chiral compound of the formula XII via the general procedure described by Evans et al, J. Amer. Chem. Soc., 112, 8215–8216 (1990).

In Step (C2), the chiral compound of formula XII is treated with a halogen, preferably $Br_2$ or $I_2$, and a base, preferably pyridine, in a suitable solvent, such as $CH_3CN$, THF, EtOAc or $CH_2Cl_2$, at $-20°$ C. to 30° C., preferably about 0° C. to 25° C., for 10 to 20 h, preferably about 20 h, to form the chiral halide XIII.

In Step (C3), the chiral halide XIII is treated with a hydride reducing agent, such as $LiBH_4$, in a suitable solvent, such as THF or $Et_2O$, at $-80°$ to 30° C., preferably starting at $-78°$ C. and continuing at 25° C., for 1 to 6 h, preferably about 3 h, to form the chiral hydride IIIa.

In the third alternative embodiment of Process D, the present invention comprises a process for preparing a compound of the formula I, wherein the chiral halide of formula (III) is a compound of the formula (IIIb), i.e., the a compound of the formula (III) wherein R is —C-

(O)R$^1$, wherein R$^1$ is as defined above. The halide of formula (IIIb) is prepared by the process shown in Reaction Scheme D.

Reaction Scheme D

Step (D1)

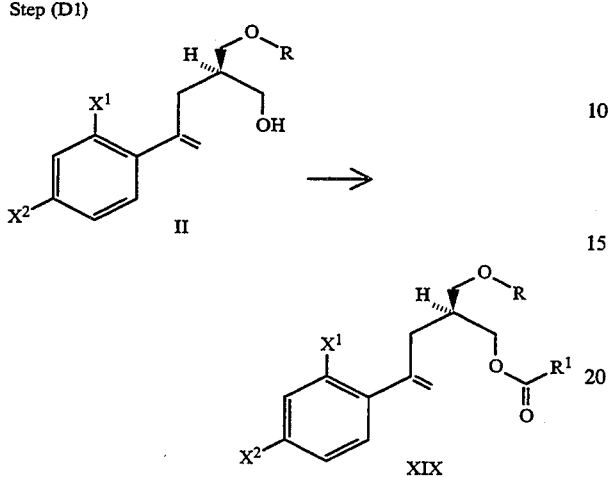

Step (D2)

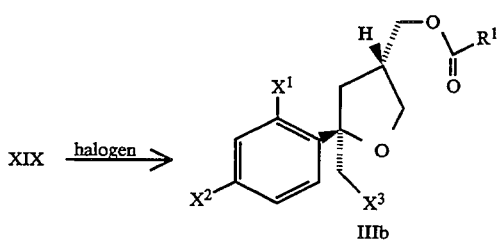

In Reaction Scheme D, Step (D1), the chiral alcohol of formula II, wherein R is —CH$_2$C$_6$H$_5$, i.e., a chiral alcohol of the formula IIb, is treated with an acylating agent, preferably acetyl chloride or acetic anhydride, in the presence of a base, such as pyridine, to form a chiral ester of the formula XIX, wherein X$^1$, X$^2$, R and R$^1$ are as defined above.

In Step (D2), the ester of the formula XIX is treated with a halogen, such as Cl$_2$, Br$_2$ or I$_2$, in a suitable solvent, such as CH$_3$CN, THF, EtOAc or CH$_2$Cl$_2$, at −20° to 30° C., preferably about 0° to 25° C., to form the halide IIIb, wherein X$^1$, X$^2$, X$^3$ and R$^1$ are as defined above.

Compounds of the formula XI can also be prepared from a compound of the formula VII by reacting with the dianion derived from acetic acid as shown below.

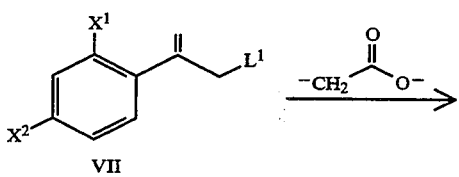

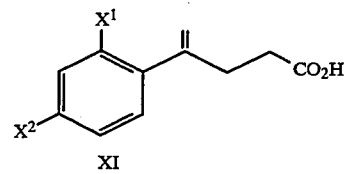

Diesters of the formula V can also be prepared from a compound of the formula XI by esterification with an alcohol of the formula R$^2$OH, wherein R is as defined above, using known methods. The resulting ester XX is deprotonated by treating with base and the resulting anion reacted with a compound of the formula R$^2$OC-(O)-L, wherein L is a halide leaving group, as defined above.

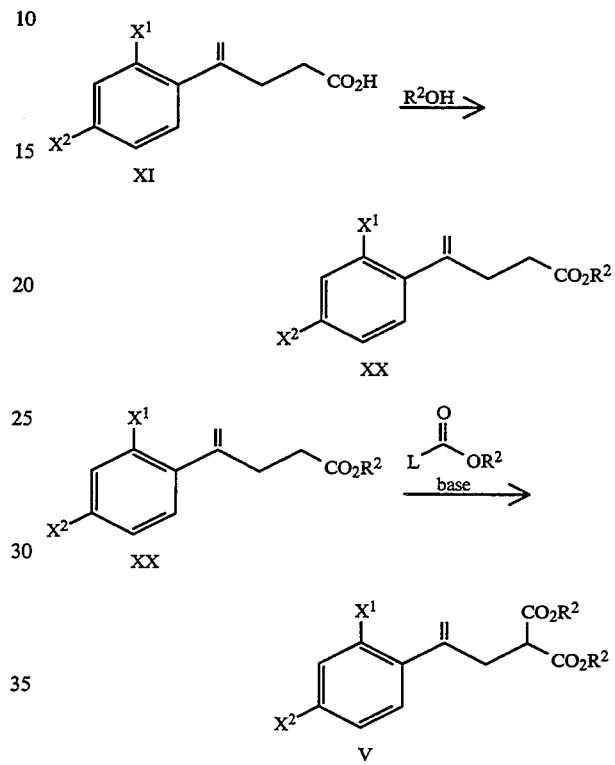

Starting compounds of the formula VI can be prepared via known methods.

The following preparations and examples illustrate the process of this invention:

PREPARATION 1

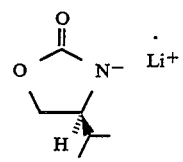

Dissolve (4S)-(−)-4-isopropyl-2-oxazolidinone (400 mg, 3.1 mmol) in 4 mL of THF and cool to −78° C. Add 2 mL (3.2 mmol) of a 1.6M solution of n-butyllithium in hexane and stir the mixture for 10 min at −78° C. to give a solution of the title oxazolidinone salt.

PREPARATION 2

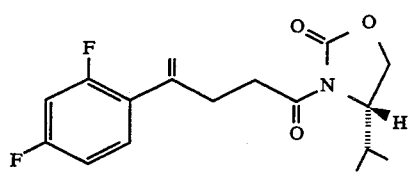

Step (a):

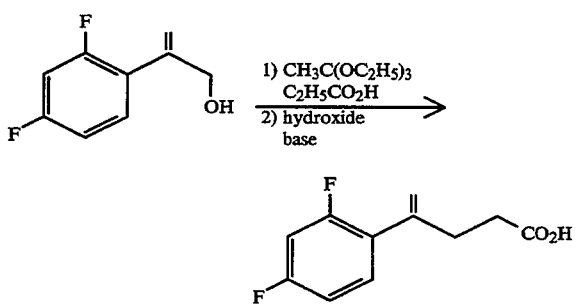

Combine the allylic alcohol (6.25 g, 31.53 mmol), triethyl orthoacetate (20.46 g, 126.12 mmol) and 5 drops of propionic acid, and heat the mixture 120° C., collecting 4 mL of EtOH by distillation. Continue heating, distilling off the excess triethyl orthoacetate (14 mL) to give a residue. Combine the residue with KOH (3.5 g, 63 mmol), 16 mL of MeOH and 4 mL of water, and stir overnight (@ 18 h) at room temperature. Dilute the mixture with water and wash with cold CH$_2$Cl$_2$, then acidify the aqueous layer to pH=3 by adding 0.1M HCl. Extract with 3 portions of EtOAc, combine the EtOAc extracts, dry over Na$_2$SO$_4$ and concentrate to give 6.75 g of the acid product. MS=213 (M+H)+

Step (b):

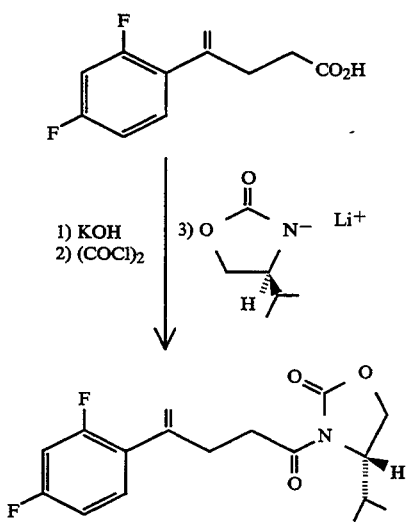

Combine the acid product of Step (a) (0.5 g, 2.36 mmol), KOH (0.13 g, 2.36 mmol) and 5 mL of EtOH, and stir for 2 h at room temperature. Evaporate the solvent to a residue, dissolve the residue in toluene and evaporate to dryness. Add 5 mL of anhydrous Et$_2$O, cool to 0° C. and add 3 mL of oxalyl chloride and 4 drops of DMF. Stir the mixture at 0° C. for 2 h, then filter and concentrate the filtrate in vacuo to a residue. Add CH$_2$Cl$_2$, then co-evaporate the CH$_2$Cl$_2$ and any residual oxalyl chloride to give the acid chloride.

Dissolve the acid chloride (2.36 mmol) in 4 mL of THF and add the resulting solution to the −78° C. solution of oxazolidinone salt from Preparation 1. Stir the mixture for 1 h, then remove the solvent in vacuo to give a residue. Chromatograph the residue (silica gel, 15%–20% EtOAc/hexane) to give 0.26 g of the title compound. MS=324 (M+H)+.

PREPARATION 3

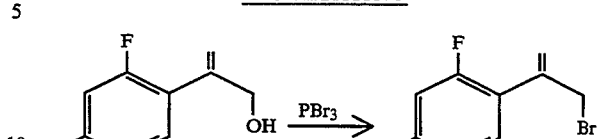

Dissolve the allylic alcohol (5.37 g, 31.58 mmol) in 50 mL of CH$_2$Cl$_2$ and cool the resulting solution to 0° to 5° C. Add PBr$_3$ (1.0 mL, 10.53 mmol), warm to room temperature and stir for 1 h, while monitoring the reaction by TLC (silica gel, 25% EtOAc/hexane). Add 50 mL of ice water, stir for 5 min, separate the layers, and dry the organic layer over MgSO$_4$. Concentrate in vacuo to give 6.45 g of the bromide product. MS=233 M+

PREPARATION 4

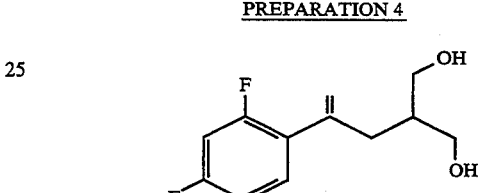

Step (a):

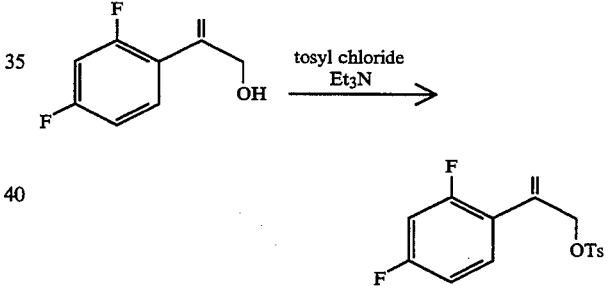

Dissolve the allylic alcohol (8.51 g, 50 mmol) in 200 mL of CH$_2$Cl$_2$, add Et$_3$N (8.36 mL, 60 mmol) and 100 mg of DMAP, then cool the mixture to 0° to 5° C. Add tosyl chloride (10.49 g, 55 mmol), then warm slowly to room temperature. Add 1 mL of MeOH, stir for 20 min, and wash with 100 mL of water, then 100 mL of brine. Dry the organic layer over MgSO$_4$, then concentrate in vacuo to give 13.1 g of the tosylate product. (Ts=—SO$_2$C$_6$H$_4$CH$_3$).

Step (b):

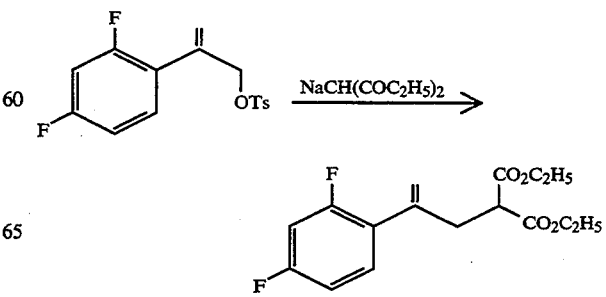

Combine diethyl malonate (1.85 g, 11.6 mmol) and 25 mL of THF, cool to 0° to 5° C., then add 0.339 g (8.48 mmol) of 60% NaH (oil dispersion) and stir the mixture at room temperature for 30 min. Add the tosylate of Step (a) (2.50 g, 7.71 mmol) and stir at room temperature for 90 min. Add 250 mL of Et₂O and 100 mL of water, stir for 10 min, separate the layers and wash the organic layer with 50 mL of brine. Dry over MgSO₄, then concentrate in vacuo to give 3.2 g of the di-ester product. MS=313 M+

Following substantially the same procedure, the allylic bromide of Preparation 3 is converted to the same di-ester product.

Step (c):

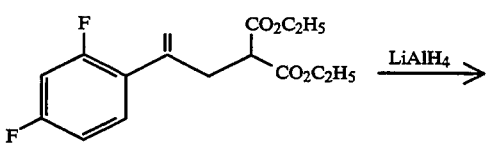

Combine the di-ester of Step (b) (1.68 g, 5.38 mmol), and 15 mL of THF and cool the mixture to 0° to 5° C. Add 7.0 mL (6.99 mmol) of a 1.0M solution of LiAlH₄ in THF dropwise over 5 min, then stir the mixture at room temperature for 2 h. Cool the mixture to 0° to 5° C., add 0.3 mL of water dropwise, then add 0.3 mL of 15% NaOH, followed by an additional 0.9 mL of water, and stir at room temperature for 1 h. Filter, concentrate the filtrate in vacuo to a residue, dissolve the residue in 50 mL of CH₂Cl₂ and dry over MgSO₄. Concentrate in vacuo to give 1.10 g of the title compound. MS=229 M+

PREPARATION 5

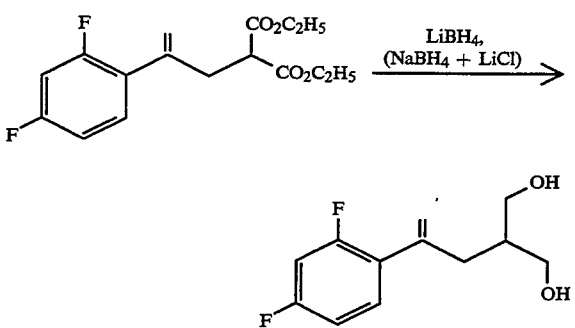

Combine the diester product of Preparation 3, Step (b) (6.77 g, 21.7 mmol), LiCl (2.76 g, 65.1 mmol) and 100 mL of EtOH, cool to 0° to 5° C., then add NaBH₄ (2.46 g, 65.1 mmol), then slowly warm the mixture to room temperature and stir overnight. Add 100 mL of MeOH and 100 mL of water, stir for 90 min, then concentrate in vacuo to a residue. Partition the residue between 500 mL of EtOAc and 100 mL of water, wash the organic layer with 100 mL of brine, dry over MgSO₄, and concentrate in vacuo to give 4.94 g of the diol product.

PREPARATION 6

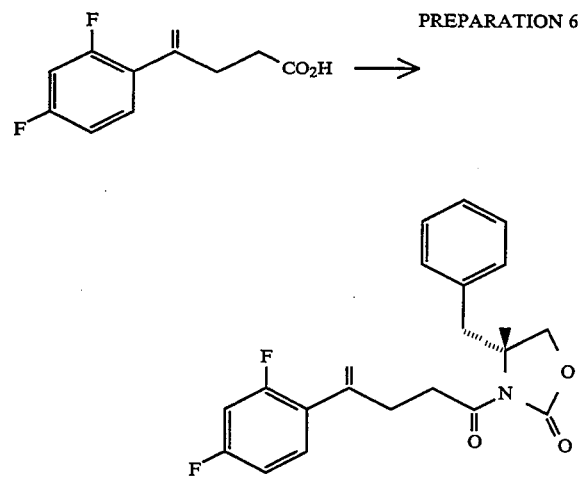

The acid of Preparation 2, Step (a) is reacted according to the general procedure taught by Evans et al, *Tetrahedron*, 44, 5525–540 (1988) and Gage et al, *Org. Syn.*, 68, 83–90 (1989) to give the chiral oxazolidinone product, $[\alpha]_D = 44.4°$ (c=1.67, CHCl₃). MS=371 (M+H)+

PREPARATION 7

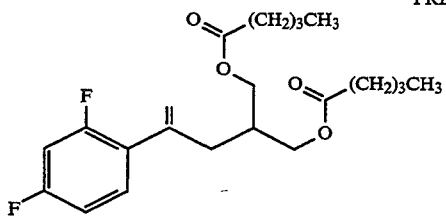

Combine 8.5 g of the diol (IV) of Preparation 4 or 5 and 50 mL THF, add 14 mL of butyric anhydride (1.15 equiv.), 15 mL Et₃N, and 0.22 g of DMAP, and stir the mixture at 20° to 23° C. for 16 h. Concentrate in vacuo to a residue, dissolve the residue in EtOAc, wash with saturated aqueous Na₂CO₃, then dry over MgSO₄. Concentrate in vacuo to give the dibutyrate product in near quantitative yield.

Using substantially the same procedure the following compound can also be prepared in near quantitative yield:

Preparation 7A

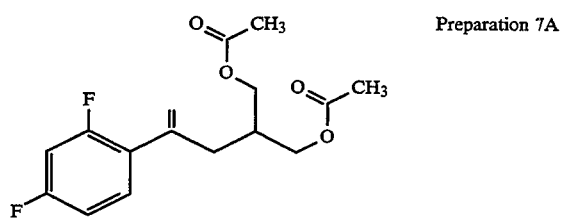

EXAMPLE 1

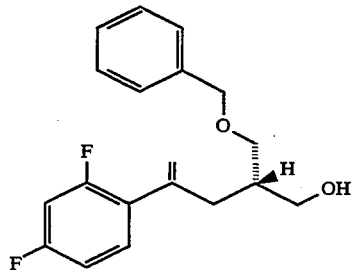

Step (a):

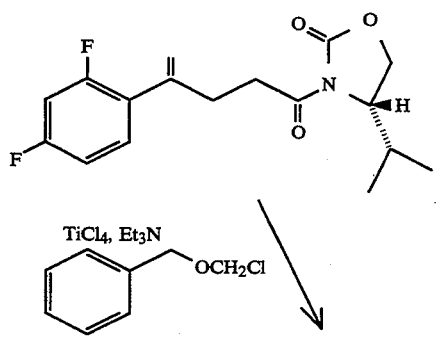

Combine the product of Preparation 2 (2.8 g, 8.66 mmol) and 12 mL of $CH_2Cl_2$ and cool the mixture to 0° C., stir the mixture, and add 9.1 mL (9.1 mmol) of a 1.0M solution of $TiCl_4$ dropwise. Stir for 5 min more. then add $Et_3N$ (1.27 mL, 9.1 mmol) dropwise and stir for 1 h at 0° C. Slowly add benzyl chloromethyl ether (3.15 g, 18.2 mmol) and stir the mixture at 0° C. for 3 h. Quench with 15 mL of saturated $NH_4Cl$, extract with $CH_2Cl_2$, dry the extract over $Na_2SO_4$, then concentrate in vacuo to a residue. Purify the residue by column chromatography (silica gel, 10% EtOAc/hexane) to give 3.21 g of the product. MS=444 (M+H)+

Step (b):

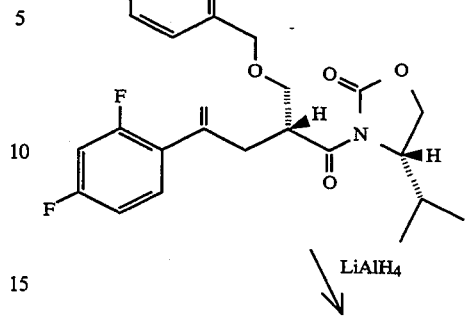

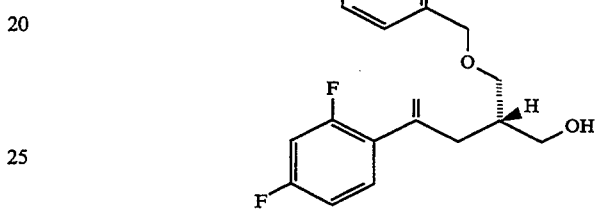

Reduce the product of Step (a) by treating with $LiAlH_4$ according to the procedure described by Evans et al., *J. Amer. Chem. Soc.*, 104, 1737–1739 (1982) to give the S-isomer of the chiral product, $[\alpha]_D = 28.4°$ (c=1.18, $CHCl_3$). MS=341 (M+Na)+

EXAMPLE 2

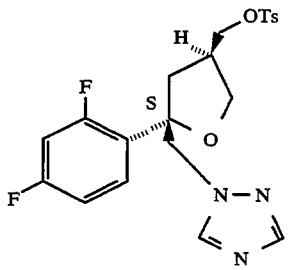

Step (a):

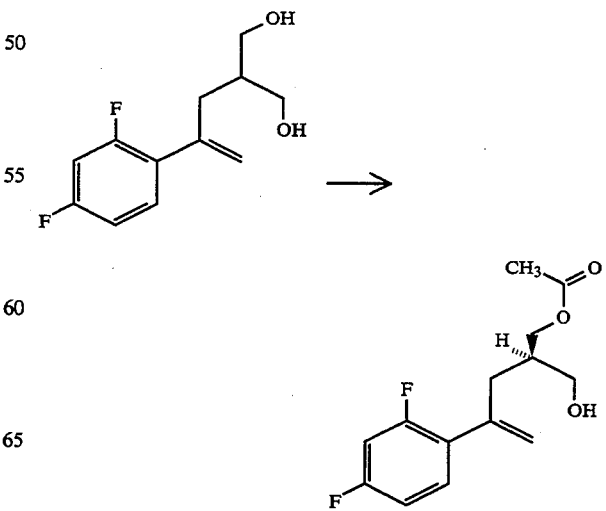

Combine the diol product of Preparation 4 or 5 (0.60 g) and 12 mL of EtOAc, add 1.8 g of porcine pancreas lipase (EC3.1.1.3), de-gas the mixture, and stir at room temperature for 48 h under nitrogen. Filter the mixture, wash the solids with EtOAc, then concentrate the combined filtrate and washings in vacuo to a residue. Purify the residue by chromatography (silica gel, 10% to 20% EtOAc/hexane) to give 0.628 g of the R-isomer of the chiral product, $[\alpha]_D = +6.2°$ (c=1.11, CHCl$_3$). MS=271 M+. 20% to 30% e.e. as determined by $^1$H NMR using a chiral shift reagent.

Step (b):

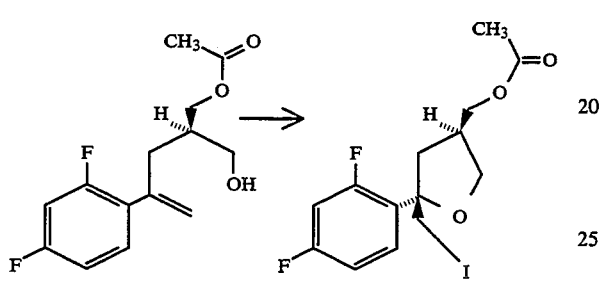

Combine the product of Step (a) (0.1 g, 0.37 mmol) and 3 mL of CH$_3$CN, add pyridine (45 μL, 0.56 mmol) and I$_2$ (0.188 g, 0.74 mmol) and stir the mixture at 0° to 5° for 6 h. Add 50 mL Et$_2$O and 25 mL of water, then add a saturated solution of Na$_2$S$_2$O$_3$ (dropwise) until the mixture is colorless. Stir for 10 min, separate the layers, dry the organic layer over Na$_2$SO$_4$, then concentrate in vacuo to a residue. Purify by preparative TLC (silica gel, 50% EtOAc/hexane) to give 0.132 mg of the chiral iodide. The product is a 90:10 mixture of cis and trans isomers by $^1$H NMR.

Step (c):

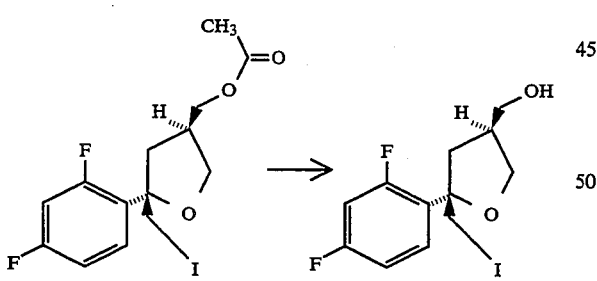

Combine the iodide product of Step (b) (0.387 g, 0.908 mmol) and 9 mL of MeOH, add water until the mixture becomes slightly cloudy, then add K$_2$CO$_3$ (0.148 g, 1.07 mmol) and stir the mixture at 0° to 5° C. for 1 h. Add CH$_2$Cl$_2$, wash with water, then dry over Na$_2$SO$_4$. Concentrate in vacuo to a residue then purify the residue by preparative TLC (silica gel, 50% EtOAc/hexane) to give 0.348 g of the chiral alcohol product (90:10 cis/trans ratio).

Step (d):

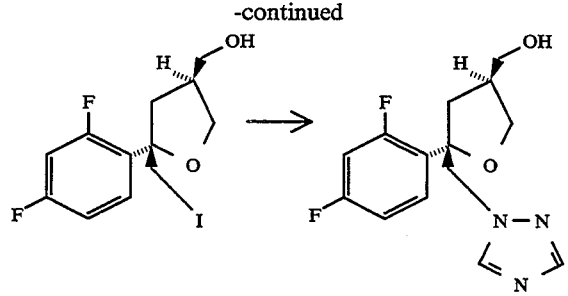

Treat the chiral alcohol product of Step (c) with sodium triazole according to the procedure of Example 3, Step (b) to give the chiral triazole product.

Step (e):

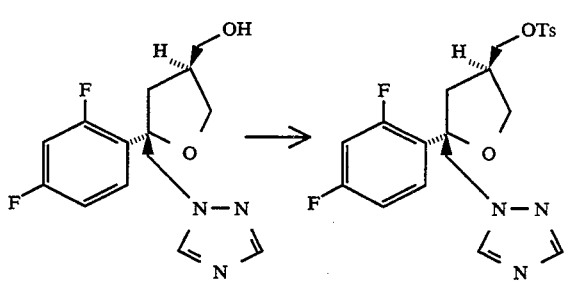

Treat the alcohol product of Step (d) with tosyl chloride and pyridine as described in Example 6, Step (d) (second paragraph) to form the S-cis isomer of the title compound, $[\alpha]_D = +9.5°$ (c=1.1, CHCl$_3$), in 25% e.e.

Where the chiral iodide of Example 2A is used in Step (c) and carried through Steps (d) and (e), title compound of high optical purity is formed, $[\alpha]_D = +37.0°$ (c=1.19, CHCl$_3$).

EXAMPLE 2A

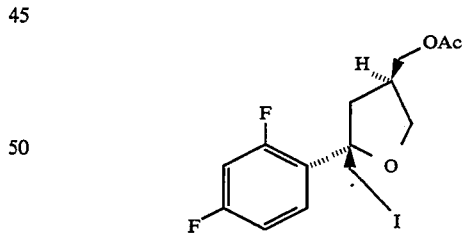

Step (a):

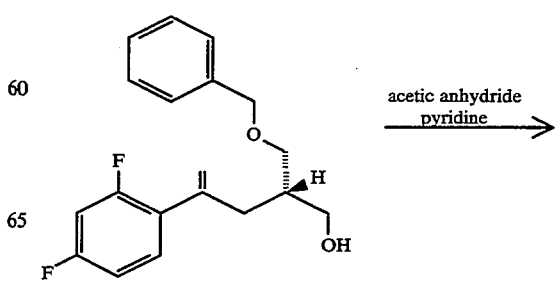

acetic anhydride
pyridine →

-continued

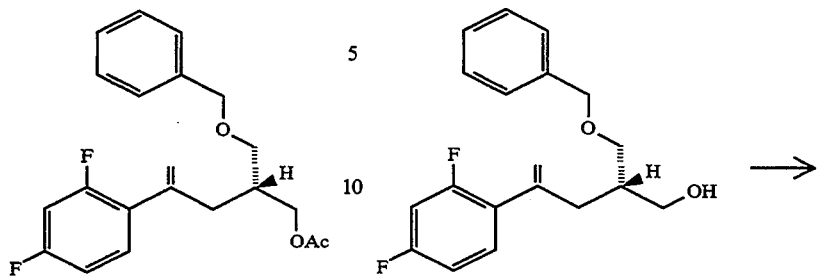

Combine the chiral product of Example 1 and acetic anhydride in $CH_2Cl_2$, add pyridine and stir at room temperature to form the chiral acetylated product.

Step (b):

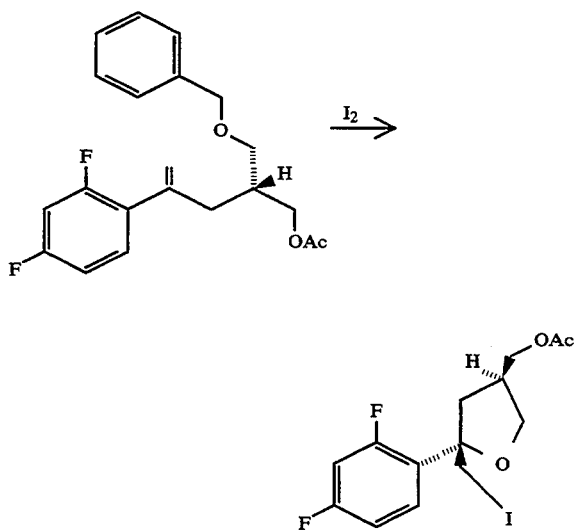

Treat the acylated product of Step (a) with $I_2$ (a base is not used) according to the procedure of Example 2, Step (b) to form the chiral iodide product.

EXAMPLE 3

Step (a):

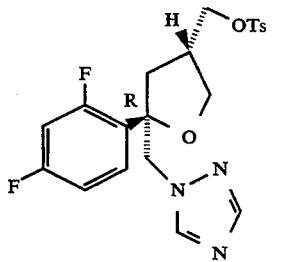

-continued

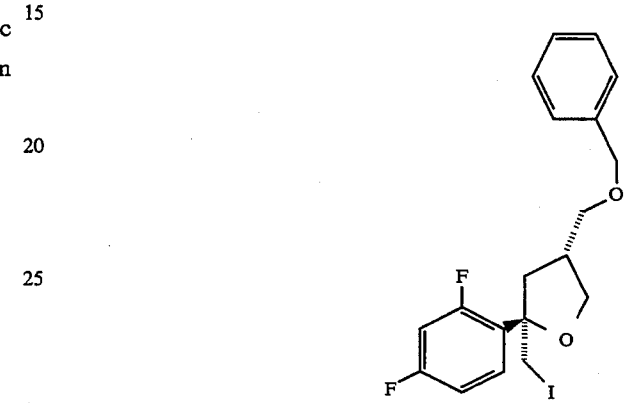

Dissolve the product of Example 1 (1.7 g, 5.34 mmol) in 12 mL of $CH_3CN$, cool the solution to 0° to 5° C. and add $I_2$ (2.8 g, 11.0 mmol) and pyridine (1.0 mL, 12.4 mmol). Stir the resulting mixture at 0° to 5° C. for 6 h, then add saturated $Na_2S_2O_3$ (aqueous) and $Et_2O$ and stir until the mixture is colorless. Extract with $Et_2O$, wash the extract with 0.01N HCl, then with saturated $NaHCO_3$, and dry over $Na_2SO_4$. Concentrate in vacuo to a residue and purify the residue by column chromatography (silica gel, 0% to 5% EtOAc/hexane) to give 2.3 g of the cyclized iodide, $[\alpha D = +3.7°$ (c=1.17, $CHCl_3$). $MS = 444 (M+H)^+$ Step (b):

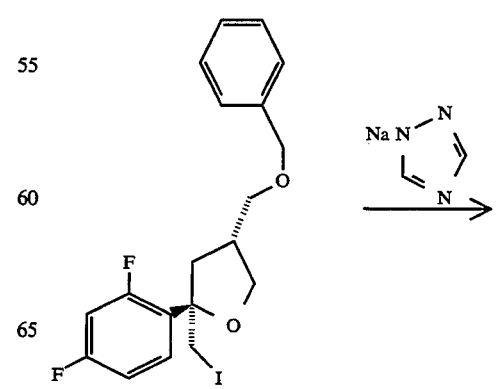

-continued

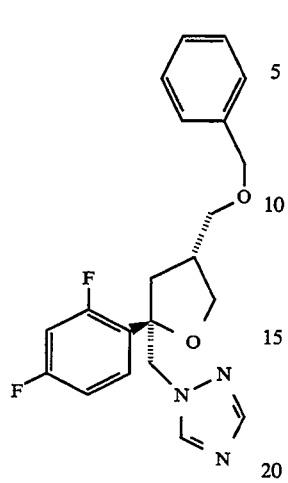

Dissolve the iodide product of Step (a) (1.18 g, 4.01 mmol) in 8 mL of DMF, then add sodium triazole (0.73 g, 8.02 mmol) and 5 drops of DMPU and heat the mixture at 100° C. for 30 h. Concentrate In vacuo to a residue, then partition the residue with 100 mL water and 100 mL EtOAc. Extract the aqueous layer with EtOAc, combine the organic layers and dry over Na$_2$SO$_4$. Concentrate in vacuo to a residue and chromatograph the residue (silica gel, 20% to 30% EtOAc/hexane) to give the R-cis triazole product, along with the R-trans isomer, i.e.,

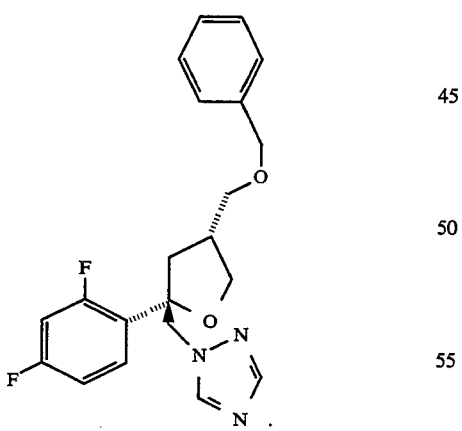

R-cis triazole, 1.0 g, [α]$_D$= −42.1° (c=1.17, CHCl$_3$). MS=386 (M+H)$^+$ R-trans triazole, 0.24 g, [α]$_D$= +10.6° (c=1.12, CHCl$_3$). MS=386 (M+H)$^+$ Step (c):

-continued

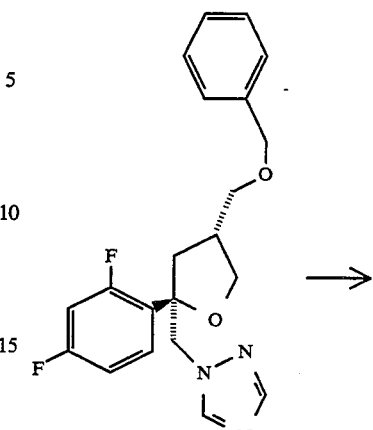

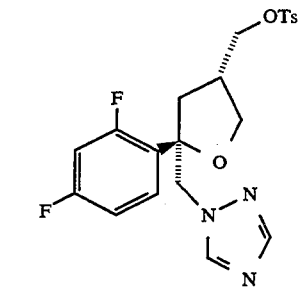

Combine the R-cis triazole product of Step (b) (0.83 g, 2.16 mmol), 0.22 g of 10% Pd on carbon, 20 mL of EtOH and 1.2 mL of 1N HCl, and agitate the mixture under 60 p.s.i. of hydrogen for 3 h. Filter, concentrate the filtrate to a residue, dissolve the residue in EtOAc and wash with aqueous NaHCO$_3$. Dry the EtOAc solution over NaSO, concentrate in vacuo to give the R-cis alcohol product.

Treat the alcohol with tosyl chloride and pyridine as described in Example 6, Step (d) (2nd paragraph) to give the R-cis isomer of the title compound, m.p.=101°-102° C., [α]$_D$= −43.9° (c=1.16, CHCl$_3$).

EXAMPLE 4

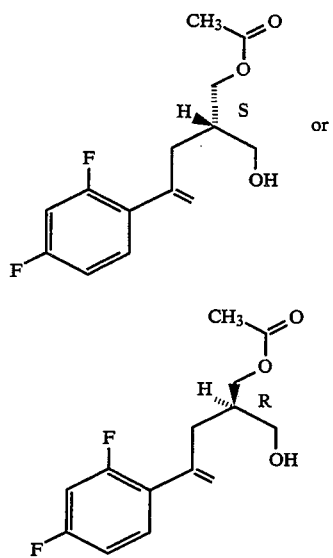

Screening of enzymes for the acetylation of the diol (IV) from Preparation 4 or 5 is carried out using a number of commercially available enzymes via the following general procedure. Combine 0.050 g of diol (IV) and 1.0 ml of toluene containing 10.0 equivalents of vinyl acetate, then add 0.04 to 0.10 g of the commercial enzyme preparation and stir the mixture at 20° to 23° C. Analyze the reaction mixture by chiral HPLC to determine: the amounts of remaining diol (IV), hydroxy acetate (IIa), and diacetate (of formula V wherein $R^2$ is $CH_3$); and the absolute configuration and e.e. of chiral hydroxy acetate (IIa). The results are summarized in Table I below.

TABLE 1

| Source & Enzyme | # mgs | Time (hr.) | IV | IIa | V | * | % e e |
|---|---|---|---|---|---|---|---|
| Amano Acylase | 53.8 | 22 | 41.12 | 55.76 | 3.12 | R | 29 |
| Amano AK | 45.2 | 3.75 | 0.29 | 93.04 | 6.66 | R | 79 |
| Amano AP-12 | 47.6 | 22 | 83.48 | 15.96 | 0.56 | R | 55 |
| Amano AY-30 | 50.3 | 3.75 | 0.18 | 58.02 | 41.80 | R | 94 |
| Amano CE | 47.7 | 3.75 | 0.36 | 92.02 | 7.62 | R | 93 |
| Amano CE | 50.0 | 1.66 | — | 100 | — | R | 97 |
| Amano CES | 46.7 | 3.75 | 5.07 | 93.81 | 1.12 | R | 71 |
| Amano D | 50.8 | 22 | 91.96 | 7.51 | 0.53 | R | 37 |
| Amano FAP-15 | 53.6 | 22 | 92.12 | 7.29 | 0.58 | R | 30 |
| Amano G | 77.4 | 22 | 2.10 | 86.98 | 10.92 | R | 66 |
| Amano GC-4 | 47.3 | 22 | 69.41 | 29.85 | 0.74 | S | 7 |
| Amano Lilipase A-10 | 56.5 | 94 | 84.85 | 15.15 | — | R | 42 |
| Amano MAP-10 | 48.1 | 22 | 49.04 | 49.55 | 1.41 | R | 69 |
| Amano N | 55.6 | 22 | 94.30 | 5.20 | 0.50 | R | 44 |
| Amano PGE | 63.1 | 22 | 85.09 | 14.06 | 0.85 | R | 7 |
| Affiano PS-30 | 51.5 | 3.75 | 0.28 | 92.02 | 7.70 | R | 77 |
| Amano R | 43.9 | 22 | 68.66 | 29.92 | 1.41 | R | 44 |
| Biocatalyst Alcaligenes sp. | 66.7 | 1.33 | — | 34.85 | 65.15 | R | 45 |
| Biocatalyst Asp. niger | 76.2 | 42.25 | 83.81 | 15.79 | 0.40 | R | 51 |
| Biocatalyst C. cylindracea | 67.4 | 1.33 | 2.28 | 74.07 | 23.65 | R | 55 |
| Biocatalyst Chr. viscosum | 55.6 | 42.25 | 67.47 | 32.31 | 0.22 | R | 45 |
| Biocatalyst H. lanugiosa | 81.2 | 1.33 | — | 98.75 | 1.25 | R | 97 |
| Biocatalyst M. javanicus | 64.3 | 42.25 | 5.03 | 88.59 | 6.38 | R | 62 |
| Biocatalyst M. meihei | 70.7 | 18 | — | 73.98 | 26.02 | R | 87 |
| Biocatalyst P. cyclopium | 63.5 | 18 | — | 58.51 | 41.49 | R | 51 |
| Biocatalyst Ps. fluorescens | 65.8 | 1.33 | — | 100 | — | R | 99 |
| Biocat. Rh. delemar | 84.1 | 18 | — | 82.30 | 17.70 | R | 69 |
| Biocatalyst Rh. japonicus | 96.3 | 42.25 | 84.95 | 15.03 | 0.02 | R | 66 |
| Biocatalyst Rh. javanicus | 135.2 | 42.25 | 88.95 | 11.05 | — | R | 36 |
| Biocatalyst Rh. niveus | 61.7 | 3.00 | 88.78 | 11.22 | — | R | 46 |
| Genzyme C. cylindracea | 23.0 | 94 | 12.10 | 65.62 | 22.28 | R | 5 |
| Gist Brocades Calf lipase | 96.3 | 94 | 58.68 | 37.12 | 4.19 | S | 8 |
| Gist Brocades Kid lipase | 135.2 | 94 | 67.55 | 26.59 | 5.86 | S | 1 |
| IBT Peptidase | 45.0 | 22 | 94.97 | 4.43 | 0.60 | S | 25 |
| ISC BE1 | 66.7 | 94 | 79.91 | 19.49 | 0.59 | R | 2 |
| ISC BP1 | 55.6 | 94 | 76.83 | 22.96 | 0.21 | R | 5 |
| ISC BP1 immob | 70.0 | 94 | 9.21 | 77.76 | 13.03 | R | 45 |
| ISC BP2 | 81.2 | 94 | 78.16 | 21.63 | 0.20 | R | 5 |
| ISC BP2 immob | 63.5 | 94 | 46.88 | 47.41 | 5.71 | S | 50 |
| ISC BP3 | 64.3 | 45.75 | 75.79 | 23.94 | 0.27 | R | 4 |
| ISC BP4 | 76.2 | 94 | 96.89 | 3.11 | — | S | 34 |
| ISC BPG1 | 65.8 | 94 | 81.62 | 18.18 | 0.20 | R | 8 |
| ISC FP1 | 65.8 | 94 | 71.40 | 28.25 | 0.35 | R | 40 |
| Meito MY | 48.3 | 3.75 | 0.15 | 65.27 | 34.58 | R | 95 |
| Meito OF | 47.1 | 3.75 | 3.00 | 86.63 | 10.37 | S | 8 |

TABLE 1-continued

| Source & Enzyme | # mgs | Time (hr.) | IV | IIa | V | * | % e e |
|---|---|---|---|---|---|---|---|
| Meito PL | 47.0 | 3.75 | — | 11.79 | 88.21 | R | 55 |
| Novo IM20 | 61.7 | 3.00 | — | 81.53 | 18.47 | R | 95 |
| Novo SP435 | 84.1 | 3.00 | — | — | 100 | — | — |
| Sigma PPL | 102.5 | 5.50 | — | 93.97 | 6.03 | R | 41 |
| Sigma Wheatgerm | 23 | 94 | 86.31 | 13.51 | 0.18 | R | 5 |
| Solvay PPL | 80.4 | 20 | 9.69 | 90.31 | — | R | 29 |
| Toyobo LPL | 9.7 | 3.75 | 2.96 | 53.66 | 43.37 | R | 29 |
| Toyobo NEP-160 | 51.8 | 94 | 68.96 | 30.71 | 0.33 | S | 41 |

*Denotes absolute configuration at the chiral center in (IIa).

EXAMPLE 4A

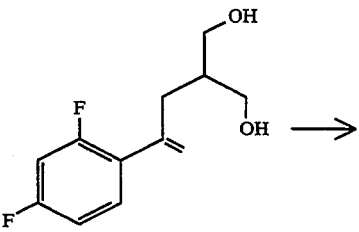

Prepare a 0.2M solution of the prochiral diol in toluene. Add the diol solution to a mixture of vinyl acetate (5 equivalents) and the commercially available enzyme Novo SP435 (Candida antarctica) and agitate the mixture at 20° to 23° C. Analyze the S hydroxy ester product as described in Example 4. The results of several such experiments, using the quantities of reagents indicated, are presented in the following table.

| diol | lipase | time (min) | % mono acetate | e.e. |
|---|---|---|---|---|
| 4.9 g | 0.54 g | 85 | 87.2 | 90% |
| 6.1 g | 0.50 g | 190 | 87.6 | 89% |
| 11.4 g* | 0.51 g | 210 | 75.6 | 94% |
| 10.7 g** | 1.0 g | 80 | 71.1 | 96% |

*This reaction was run using a 0.4M diol solution in toluene
**This reaction was run using molecular seives to dry the diol toluene solution.

The reaction is also run in a variety of solvents, at a temperature of 0° to 35° C., via substantially the same procedure as described above to give the following results.

| Solvent | vinyl acetate # equiv | diol/enzyme ratio g/g | Temp. °C. | IV | IIa | V | % e.e |
|---|---|---|---|---|---|---|---|
| iPr$_2$O | 10.0 | 4.0 | 0 | 5.76 | 83.85 | 10.39 | 91 |
| THF | 10.0 | 4.0 | 0 | 2.41 | 80.65 | 16.93 | 87 |
| Dioxane | 10.0 | 4.0 | 20–23 | 1.01 | 74.71 | 24.26 | 93 |
| CH$_3$CN | 10.0 | 4.0 | 0 | 0 | 77.06 | 22.94 | 98 |
| Acetone | 10.0 | 4.0 | 0 | 1.19 | 83.07 | 15.74 | 94 |
| Toluene | 10.0 | 4.0 | 0 | 0.86 | 89.21 | 9.93 | 93 |

-continued

| Solvent | vinyl acetate # equiv | diol/ enzyme ratio g/g | Temp. °C. | product composition (%) | | | % e.e |
|---|---|---|---|---|---|---|---|
| | | | | IV | IIa | V | |
| tAmyl Alcohol | 5.0 | 4.0 | 0 | 35.04 | 57.56 | 7.40 | 91 |

EXAMPLE 4B

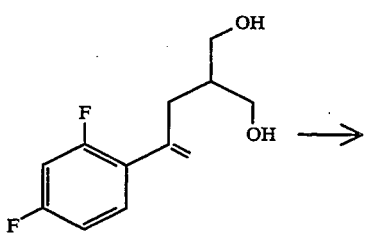

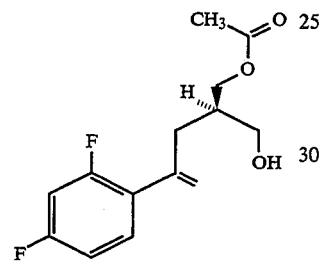

The reaction was run using the commercially available enzyme Amano CE (*Humicloa lanugiosa*) according to the procedure of Example 4A to form the R hydroxy ester. The results of several such experiments are presented in the following table.

| diol | lipase | time (min) | % mono acetate | e.e. |
|---|---|---|---|---|
| 0.05 g | 0.05 g | 95 | 97 | 99% |
| 5.3 g | 5.0 g | 95 | 97.3 | 96% |
| 1.0 g | 0.1 g** | 930 | 92.8 | 91% |
| 5.0 g | 5.0 g | 170 | 97.6 | 97% |
| 7.7 g | 1.0 g** | 170 | 91.3 | 95% |

**The enzyme used in these experiments was recovered from a previous run and re-used.

EXAMPLE 5

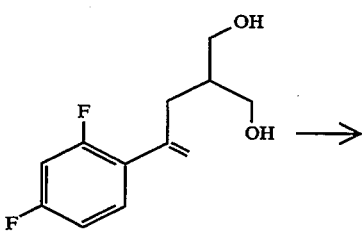

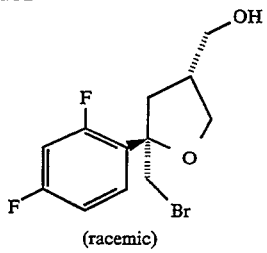
(racemic)

Combine the diol product of Preparation 4 or 5 (0.5 g, 2.19 mmol) and 10 mL of CH$_2$Cl$_2$, cool to 0° to 5° C., then add Br$_2$ (0.112 mL, 2.19 mmol) and pyridine (0.117 mL, 2.19 mmol) and stir the mixture at 0° to 5° C. for 18 h. Add 25 mL of CH$_2$Cl$_2$, wash successively with 10 mL of 10% Na$_2$SO$_3$, 10 mL of 1N HCl, and 10 mL of NaHCO$_3$, then dry over MgSO$_4$. Concentrate in vacuo to a residue and chromatograph the residue (silica gel, 10% EtOAc/hexane) to give 0.59 g of the bromide product. MS=307 M+

EXAMPLE 6

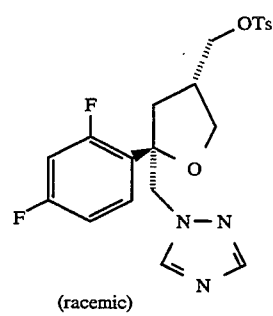
(racemic)

Step (a):

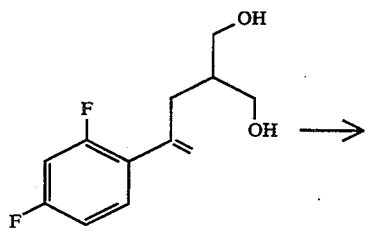

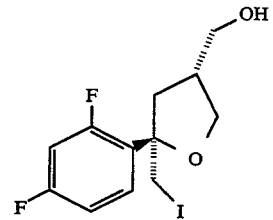

Combine the diol product of Preparation 4 or 5 (3.80 g, 16.6 mmol), 50 mL of CH$_3$CN and 2.0 mL (25.0 mmol) of pyridine, cool the mixture to 0° to 5° C., then add I$_2$ (8.45 g, 33.3 mmol) and stir at 0° to 5° C. for 1 h. Add 500 mL of Et$_2$O and 100 mL of 10% Na$_2$SO$_3$, stir for 5 min, then separate the layers. Wash the organic layer with 50 mL of 1N HCl, 50 mL of 5% NaHCO$_3$, and 50 mL of brine, then dry over MgSO$_4$. Concentrate in vacuo to a residue and chromatograph the residue (silica gel, 10% EtOAc/hexane) to give 5.10 g of the racemic iodide product. MS=354 M+. $^1$H NMR indicates the product is a 84%/16% mixture of trans and cis isomers.

Step (b):

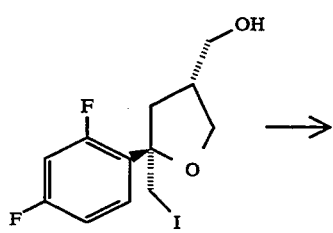

Combine the iodide product of Step (a) (5.00 g, 14.1 mmol) and 50 mL of $CH_2Cl_2$, add 3,4-dihydro-2H-pyran (1.93 mL, 21.2 mmol) and 0.1 g of p-TSA monohydrate, then stir the mixture at room temperature for 2 h. Add 100 mL of $CH_2Cl_2$, wash with 50 mL of 5% $Na_2CO_3$ and 50 mL of water, then dry over $MgSO_4$. Concentrate in vacuo to a residue and chromatograph (silica gel, 2.5% EtOAc/hexane) to give 5.61 g of the racemic THP ether product. MS=439 M+

Step (c):

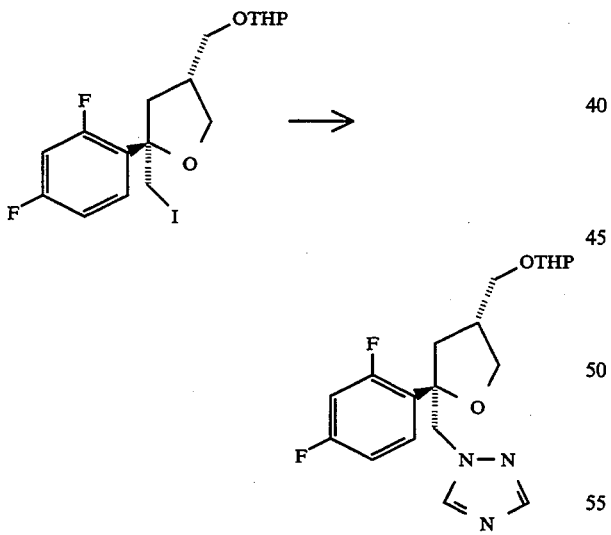

Combine the THP ether product of Step (b) (5.54 g, 12.6 mmol) and 60 mL of DMF, add 90% sodium 1,2,4-triazole (2.30 g, 25.2 mmol) and 5 drops of DMPU, then heat the mixture at 90° to 100° C. for 48 h. Cool the mixture to room temperature, concentrate in vacuo to a residue, and partition the residue in 100 mL of water and 100 mL of EtOAc. Extract the water layer with 100 mL of EtOAc, dry the combined EtOAc layers over $MgSO_4$, concentrate in vacuo to a residue, then chromatograph the residue (silica gel, EtOAc) to give 4.17 g of the racemic triazole product. MS=380 M+

Step (d):

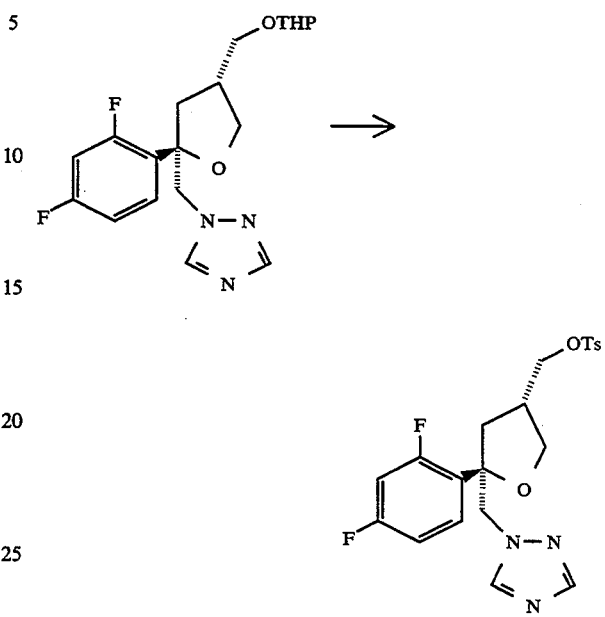

Combine the triazole product of step (c) (4.10 g, 12.2 mmol) and 50 mL of 10% HCl and stir at room temperature for 18 h. Concentrate in vacuo to a residue, dissolve the residue in 150 mL $CH_2Cl_2$ and 50 mL of water, then add 10% $Na_2CO_3$ (dropwise) to adjust the aqueous layer to pH=8. Separate the layers, wash the organic; layer with 50 mL of brine, dry over $MgSO_4$, then concentrate in vacuo to give 3.02 g of the alcohol.

Combine the alcohol and 30 mL of pyridine, cool the mixture to 0° to 5° C., and add tosyl chloride (2.13 g, 11.1 mmol). Stir the mixture at 0° to 5° C. for 18 h, then at room temperature for 18 h. Concentrate in vacuo to a residue, dissolve the residue in 100 mL of $CH_2Cl_2$, wash with 50 mL of water, 50 mL of 5% $NaHCO_3$, and 50 mL of brine, then dry over $MgSO_4$. Concentrate in vacuo to a residue and chromatograph (silica gel, EtOAc) to give 3.13 g of the racemic title compound. MS=450 M+

EXAMPLE 7

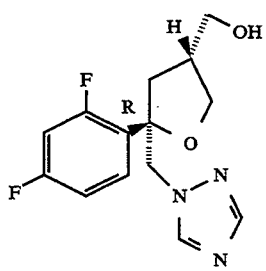

Step (a):

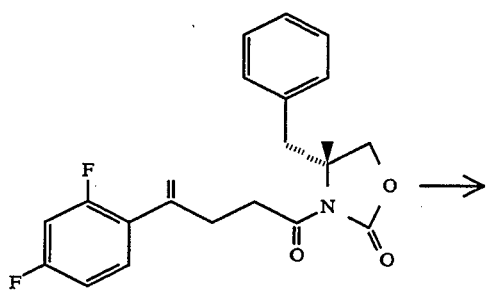

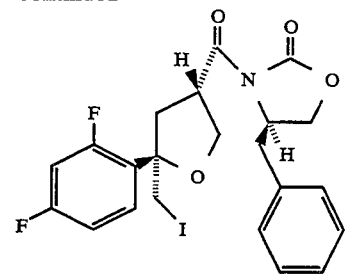

Combine the product of Step (a) (1 g, 2.5 mmol), 0.45 mL of pyridine and 20 mL of CH₃CN, cool to 0° C., then add 1.78 g of I₂. Stir the mixture a room temperature for 20 h, then quench the reaction with dilute aqueous Na₂S₂O₄. Extract with Et₂O (2×20 mL), combine the extracts and dry over MgSO₄. Concentrate in vacuo to a residue then chromatograph (silica gel, 15% to 25% EtOAc/hexane) to give 1.18 g of the chiral iodide product (89.8% yield). MS=528 (M+H)⁺

Step (c):

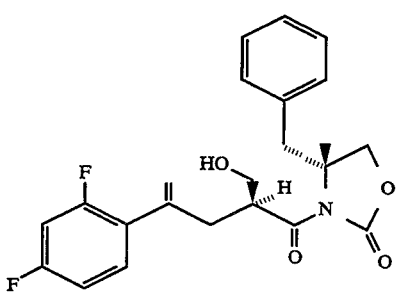

Essentially following the procedure described by Evans et al, *J. Amer. Chem. Soc.*, 112, 8215–8216 (1990), combine the oxazolidinone product of Preparation 6 (2.18 g, 5.88 mmol) and 24 mL of CH₂Cl₂ at 0° C., add 6.5 mL of 1M TiCl₄ in CH₂Cl₂. Stir for 5 min, then add 1.12 mL of Hünigs base and stir at 0° C. for 30 min. Add a solution of 1,3,5-trioxane (0.67 g, 7.44 mmol) in 5 mL of CH₂Cl₂, then add another 6.5 mL of 1M TiCl₄ in CH₂Cl₂ and stir at 0° to 3° C. for 2.5 h. Add 10 mL of saturated NH₄Cl and stir for 5 min, then separate the layers and extract the aqueous phase with 20 mL CH₂Cl₂. Combine the organic phase and the extract, wash with brine, dry over MgSO₄, then concentrate in vacuo to a residue. Chromatograph the residue (silica gel, 15% to 25% EtOAc/hexane) to give 1.33 g of the chiral product, [α]$_D$= −62.9° (c=1.7, CHCl₃). MS=402 (M+H)⁺

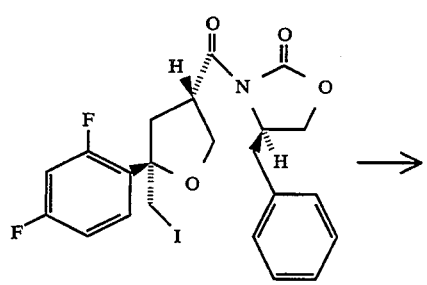

Combine the iodide product of Step (b) (0.9 g, 1.71 mmol) and 35 mL of THF and cool to −78° C., then add 0.85 mL of 2M LiBH₄ in THF and stir the mixture for 1 h while warming to room temperature. Stir for 2 h at room temperature, then cool to −10° C. and quench by adding saturated aqueous NH₄Cl. Stir for 0.5 h, concentrate in vacuo to a residue, partition the residue between CH₂Cl₂ and water, separate the layers and dry the organic layer over MgSO₄. Concentrate in vacuo to a residue and chromatograph (silica gel, 15% to 30% EtOAc) to give 0.43 g of the chiral product. MS=355 (M+H)⁺

Step (d):

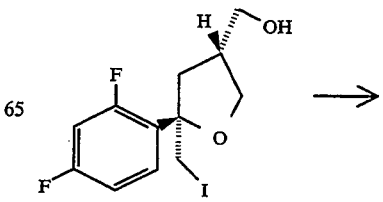

Step (b):

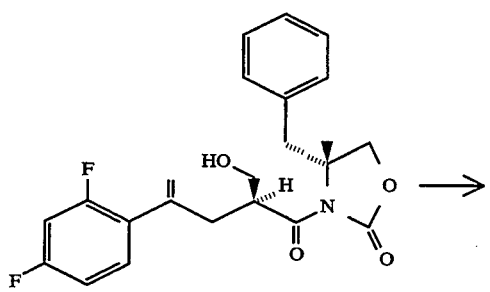

-continued

Step (d):

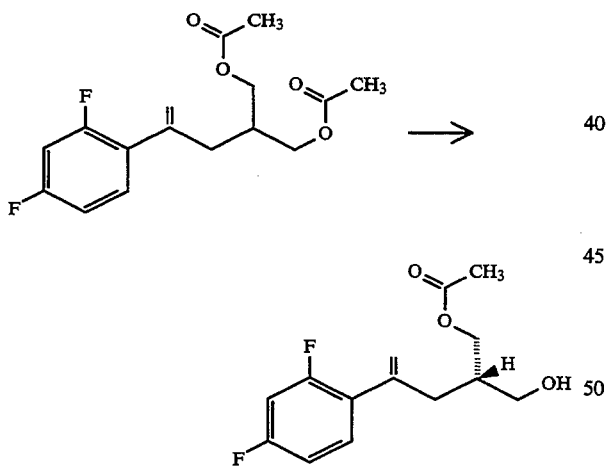

Combine the product of Step (c) (0.3 g, 0.85 mmol), sodium triazole (0.86 g, 8.5 mmol) and 5 mL of DMF and heat at 80° C. under nitrogen for 24 h. Cool the mixture, dilute With 50 mL of water and extract with $CH_2Cl_2$ (2×40 mL). Combine the extracts, wash with brine, dry over $MgSO_4$, then concentrate in vacuo to a residue. Chromatograph the residue (silica gel, 50% to 75% EtOAc) to give 0.101 g of the title compound. MS=296 (M+H)+

Unreacted starting material (0.138 g) was also recovered.

EXAMPLE 8

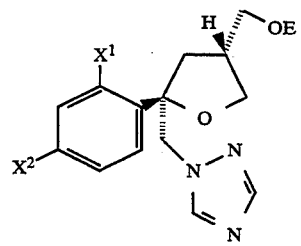

↓

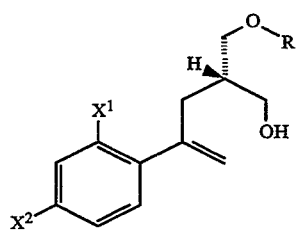

Prepare a 50 mM solution of KCl in 20% THF/water. Using this solution, prepare 5 mL of a 0.2M solution of the diacetate product of Preparation 7A. (The pH of the resulting solution is maintained at 7.5 by titration with aqueous NaOH, as needed, throughout the course of the reaction. Add 0.12 g of Amano CE and stir at room temperature for 18 h. Filter the mixture, wash the filtrate with water, aqueous $Na_2CO_3$, then brine, and dry over $MgSO_4$. Concentrate in vacuo to give the chiral product in 98% e.e., as determined by chiral HPLC.

EXAMPLE 9

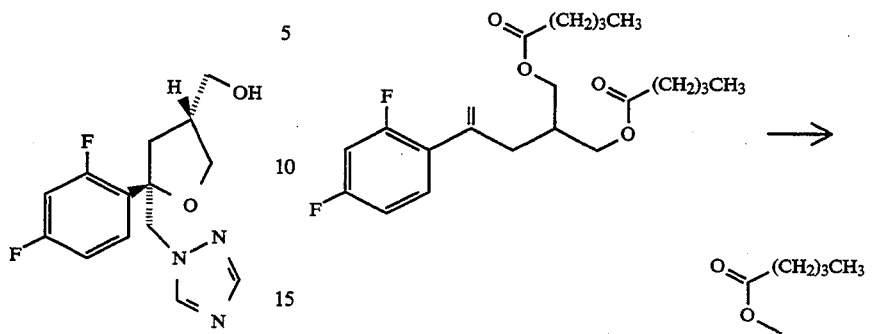

Prepare a solution of 7.0 g of the dibutyrate of Preparation 7 in 63 mL of a 50 mM solution of KCl in 20% THF/water. Add 5.0 g of Amano CE and stir the mixture at 22° C., while maintaining the pH at 7.5 by titration with aqueous NaOH using a pH stat, for 6.5 h. Extract the mixture to give an 81.5% yield of the S product in 99% e.e.

We claim:

1. A process for preparing compounds of the formula (I)

(I)

wherein: $X^1$ and $X^2$ are independently F or Cl; and E is $-SO_2R^2$, wherein $R^2$ is $C_1$-$C_6$ alkyl, $-C_6H_4CH_3$ or $-CF_3$; comprising the steps:

(a) cyclizing a chiral alcohol of the formula (II)

(II)

wherein $X^1$ and $X^2$ are as defined above, and R is a hydroxy protecting group selected from $-CH_2-C_6H_5$, tetrahydropyran-2-yl or $-C(O)R^1$, wherein $R^1$ is $C_1$-$C_6$ alkyl, by treating with a halogen and a base to form a chiral halide of the formula (III)

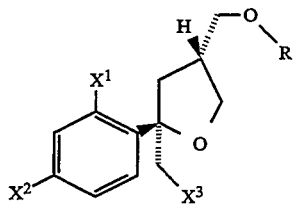

(III)

wherein X¹, X² and R are as defined above, and X³ is Cl, Br or I; and (b) treating the halide of formula (III) of step (a) with an alkali metal triazole to form a chiral triazole compound of the formula (III), wherein X³ is triazolyl; removing the protecting group R from the triazole compound to form an alcohol of the formula (III), wherein X is triazolyl and R is H; and treating the alcohol with a compound of the formula E—X, wherein X is Cl or Br, and E is as defined above, to form the compound of formula (I); or (bi) removing the protecting group R from the halide of formula (III) of Step (a) to form an alcohol of the formula (III), wherein R is H; treating the alcohol with an alkali metal triazole to form a chiral triazole compound of the formula (III), wherein X³ is triazolyl and R is H; and treating the alcohol with a compound of the formula E—X, wherein X is Cl or Br, and E is as defined above, to form the compound of formula (I).

2. A process according to claim 1 wherein R is —C(O)R¹, and the starting compound of formula (II) of Step (a) is prepared by selectively esterifying a prochiral diol of the formula (IV)

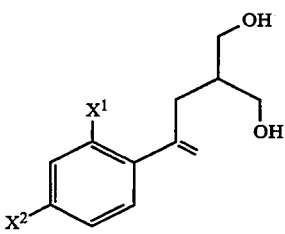

(IV)

by reacting the diol (IV) with an effective amount of a mild acylating agent in the presence of an enzyme to form the chiral hydroxy ester of formula (IIa)

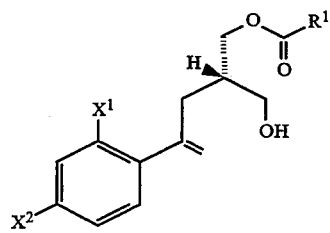

(IIa)

wherein X¹ and X² are as defined above, and R¹ is C₁-C₆ alkyl.

3. A process according to claim 1 wherein R is —C(O)R¹, and the chiral hydroxy ester of formula (II) of Step (a) is prepared by a process comprising the steps:

(i) esterifying the prochiral diol of formula (IV) with an amount of an acylating agent effective to form a diester of the formula (V)

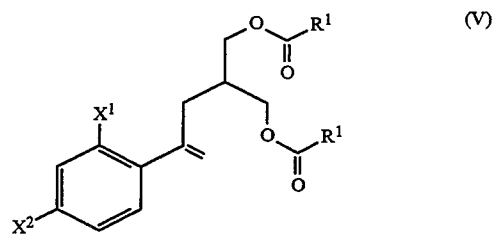

(V)

wherein X¹, X² and R¹ are as defined above; and (ii) stereoselectively hydrolyzing the diester of formula (V) of step (i) in the presence of an enzyme to form a chiral hydroxy ester of the formula (IIa)

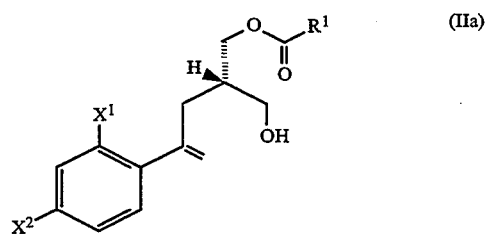

(IIa)

wherein X¹, X² and R¹ are as defined above.

4. A process according to claim 2 wherein the prochiral diol of the formula (IV) is prepared via a process comprising the steps:

(A1) converting an allylic alcohol of the formula (VI)

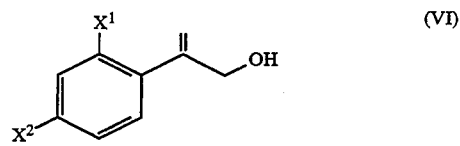

(VI)

wherein X¹ and X² are as defined above, to a compound of the formula (VII)

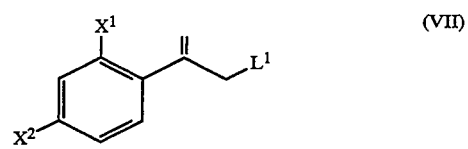

(VII)

wherein X¹ and X² are as defined above and L¹ is a leaving group selected from Br, —OSO₂CH₃ and —O-SO₂C₆H₄CH₃;

(A2) reacting the product of Step (A1) with an amount of an alkali metal salt of the anion derived from a di(C₁-C₆ alkyl)malonate effective to form a diester of the formula (VIII)

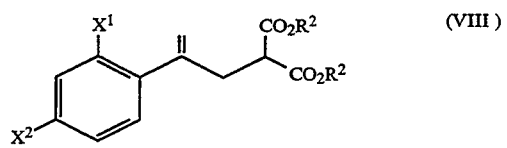

(VIII)

wherein X¹ and X² are as defined above, and R² is $C_1$–$C_6$ alkyl;

(A3) treating the diester of the formula (VIII) of Step (A2) with an amount of a hydride reducing agent effective to form the prochiral diol of the formula (IV).

5. A process according to claim 3 wherein the prochiral diol of the formula (IV) is prepared via a process comprising the steps:

(A1) converting an allylic alcohol of the formula (VI)

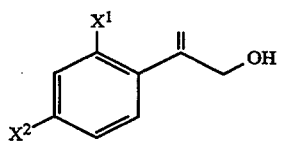

(VI)

wherein X¹ and X² are as defined above, to a compound of the formula (VII)

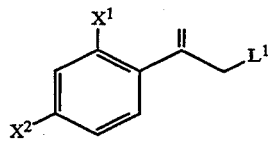

(VII)

wherein X¹ and X² are as defined above and L¹ is a leaving group selected from Br, —$OSO_2CH_3$ and —$OSO_2C_6H_4CH_3$;

(A2) reacting the product of Step (A1) with an amount of an alkali metal salt of the anion derived from a di($C_1$–$C_6$ alkyl)malonate effective to form a diester of the formula (VIII)

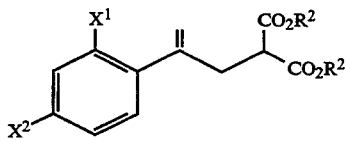

(VIII)

wherein X¹ and X² are as defined above, and R² is $C_1$–$C_6$ alkyl;

(A3) treating the diester of the formula (VIII) of Step (A2) with an amount of a hydride reducing agent effective to form the prochiral diol of the formula (IV).

6. A process according to claim 1 wherein the chiral alcohol of formula (II) of Step (a), wherein R is —$CH_2$—$C_6H_5$, is prepared by a process comprising the steps:

(B1) reacting a compound of the formula (IX)

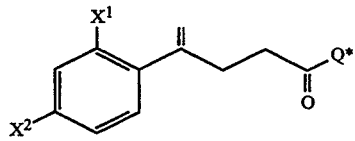

(IX)

wherein X¹ and X² are as defined above and Q* is a chiral auxiliary group, with a compound of the formula $C_6H_5$—$CH_2$—O—$CH_2$—L, wherein L is a leaving group selected from Cl, Br and I, in the presence of $TiCl_4$ and a tertiary amine base, in amounts effective to form a chiral compound of the formula (X)

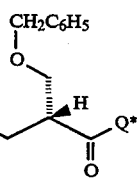

(X)

wherein X¹, X² and Q* are as defined above; and (B2) treating the product of formula (X) of Step (B1) with an amount of $LiAlH_4$ effective to form a chiral compound of the formula (II) wherein R is —$CH_2C_6H_5$.

7. A process according to claim 6 wherein the starting compound of the formula (IX)

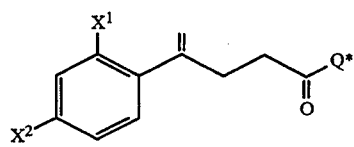

(IX)

is prepared by a process comprising the steps:

(B3) heating an allylic alcohol of the formula (VI)

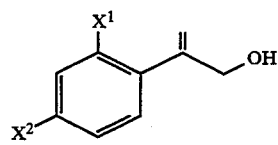

(VI)

wherein X¹ and X² are as defined above, with effective amounts of $CH_3C(OC_2H_5)_3$ and $C_2H_5CO_2H$, followed by treatment with an amount of a hydroxide base effective to form an acid of the formula (XI)

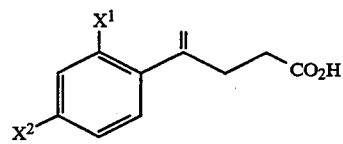

(XI)

wherein X¹ and X² are as defined above; and (B4) treating the acid of formula (XI) of step (B3) with an effective amount of an activating agent, then with an alkali metal salt of the formula $M^+$ $^-Q^*$, wherein $M^+$ is an alkali metal cation and $^-Q^*$ is the anion derived from a compound of the formula HQ*, wherein Q* is as defined above, to form a compound of the formula (IX).

8. A process for preparing compounds of the formula (I)

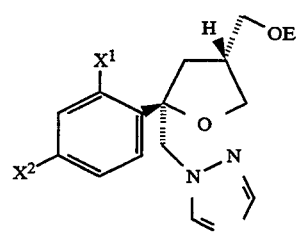

(I)

wherein: $X^1$ and $X^2$ are independently F or Cl: and E is $-SO_2R^2$, wherein $R^2$ is $C_1-C_6$ alkyl, $-C_6H_4CH_3$ or $-CF_3$: comprising the steps:

(D1) esterifying a chiral alcohol of the formula (II)

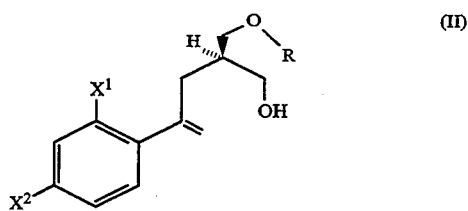

wherein $X^1$ and $X^2$ are as defined above, and R is $-CH_2-C_6H_5$, by treating with an effective amount of an acylating agent to form a chiral compound of the formula (XIX)

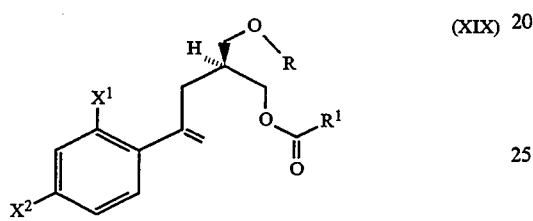

wherein $X^1$, $X^2$ and R are as defined above and $R^1$ is $C_1-C_6$ alkyl;

(D2) cyclizing the chiral product of formula (XIX) of Step (D1) by treating with a halogen to form a chiral halide of the formula (III)

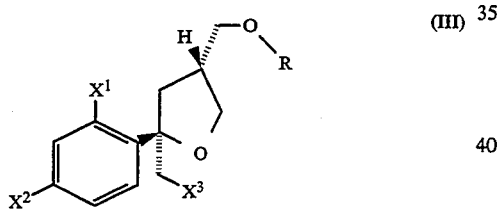

wherein $X^1$, $X^2$ are as defined above, R is $-C(O)R^1$, $R^1$ is as defined above and $X^3$ is Cl, Br or I; and (b) treating the halide of formula (III) of step (D2) with an alkali metal triazole to form a chiral triazole compound of the formula (III), wherein $X^3$ is triazolyl: removing the protecting group R from the triazole compound to form an alcohol of the formula (III), wherein X is triazolyl and R is H; and treating the alcohol with a compound of the formula E—X, wherein X is Cl or Br, and E is as defined above, to form the compound of formula (I); or (bi) removing the protecting group R from the halide of formula (III) of Step (a) to form an alcohol of the formula (III), wherein R is H; treating the alcohol with an alkali metal triazole to form a chiral triazole compound of the formula (III), wherein $X^3$ is triazolyl and R is H; and treating the alcohol with a compound of the formula E—X, wherein X is Cl or Br, and E is as defined above, to form the compound of formula (I).

9. A process according to claim 1 wherein:
(a) in Step (a): the halogen is $Br_2$ or $I_2$; the base is pyridine or $NaHCO_3$; and the cyclization is carried out in the presence of a solvent selected from $CH_3CN$, tetrahydrofuran, ethyl acetate and $CH_2Cl_2$; and (b) in Step (b):
(1) the alkali metal triazole is sodium triazole, and the triazole treatment is carried out in the presence of DMPU and N,N-dimethylformamide at 70° to 100° C.; and (2) the protecting group R is removed from the triazole compound by:
(i) where R is $-C(O)R^1$, and $R_1$ is $C_1-C_6$ alkyl, treating with a base selected from $K_2CO_3$, $Na_2CO_3$ and $NH_4OH$, in the presence of methanol and water at 0° to 25° C.; or
(ii) where R is tetrahydropyran-2-yl, treating with HCl and water at 15° to 35° C.; or
(iii) where R is $-CH_2C_6H_5$, hydrogenating in the presence of a Pd on carbon catalyst, an acid, and ethanol; to form the alcohol wherein R is H and $X^3$ is triazolyl; or (b1) in Step (b1):
(1) the protecting group R is removed by:
(i) where R is $-C(O)R^1$, and $R_1$ is $C_1-C_6$ alkyl, treating with a base selected from $K_2CO_3$, $Na_2CO_3$ and $NH_4OH$, in the presence of methanol and water at 0° to 25° C.; or
(ii) where R is tetrahydropyran-2-yl, treating with HCl and water at 15° to 35° C.; or
(iii) where R is $-CH_2C_6H_5$, hydrogenating in the presence of a Pd on carbon catalyst, an acid, and ethanol; and (2) the alkali metal triazole is sodium triazole, and the triazole treatment is carried out in the presence of DMPU and N,N-dimethylformamide at 70° to 100° C.; to form the alcohol wherein R is H and $X^3$ is triazolyl; and (3) the treatment with E—X is carried out in the presence of pyridine, and X is Cl.

10. A process according to claim 2 wherein: the mild acylating agent is selected from vinyl acetate, isopropenyl acetate, methyl acetate and ethyl acetate; and the enzyme is selected from Amano CE (*Humicloa lanugiosa*), Amano AY-30, Biocatalysts *H. lanugiosa*, Biocatalysts *M. meihei*, Biocatalysts *Ps. fluorescens*, Meito MY, Meito PL, Novo Lipozyme IM-20, and Novo SP435 (*Candida antartica*).

11. A process according to claim 3 wherein: the acylating agent is selected from butyric anhydride, acetic anhydride or acetyl chloride; and the enzyme is selected from Amano CE (*Humicloa lanugiosa*), Amano AY-30, Biocatalysts *H. lanugiosa*, Biocatalysts *M. meihei*, Biocatalysts *Ps. fluorescens*, Meito MY, Meito PL, Novo Lipozyme IM-20, and Novo SP435 (*Candida antartica*).

12. A process according to claim 4 wherein:
in Step (A1), the converting is effected by treating with a brominating agent or a sulfonylating agent;
in Step (A2), the alkali metal salt is a sodium salt and the dialkylmalonate is diethylmalonate; and
in Step (A3), the hydride reducing agent is $LiAlH_4$ or $LiBH_4$.

13. A process according to claim 5 wherein:
in Step (A1), the converting is effected by treating with a brominating agent or a sulfonylating agent;
in Step (A2), the alkali metal salt is a sodium salt and the dialkylmalonate is diethylmalonate; and
in Step (A3), the hydride reducing agent is $LiAlH_4$ or $LiBH_4$.

14. A process according to claim 6 wherein in Step (B1), L is Cl, the tertiary amine base is triethylamine, and the chiral auxiliary Q* is an oxazolidinone of the formula

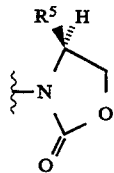

wherein $R^5$ is isopropyl.

15. A process according to claim 7 wherein: in Step (B3), the hydroxide base is KOH or NaOH; and in step (B4), the activating agent is oxalyl chloride or $SOCl_2$, $M^+$ is $Li^+$, and $-Q^+$ is

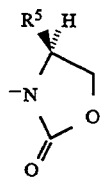

wherein $R^5$ is isopropyl.

16. A process according to claim 8 wherein: in Step (D1), the acetylating agent is acetic anhydride; and in Step (D2), the halogen is $I_2$.

* * * * *